US010422779B2

(12) United States Patent
Han et al.

(10) Patent No.: US 10,422,779 B2
(45) Date of Patent: Sep. 24, 2019

(54) CARBON DIOXIDE CHEMICAL SENSOR HAVING AMINO ACID-BASED COMPOUND AND CARBON DIOXIDE DETECTION METHOD USING THE SAME

(71) Applicant: GWANGJU INSTITUTE OF SCIENCE AND TECHNOLOGY, Gwangju (KR)

(72) Inventors: Min-Su Han, Gwangju (KR); Seung-Yoon Kang, Gwangju (KR)

(73) Assignee: GWANGJU INSTITUTE OF SCIENCE AND TECHNOLOGY, Gwangju (KR)

( * ) Notice: Subject to any disclaimer, the term of this patent is extended or adjusted under 35 U.S.C. 154(b) by 225 days.

(21) Appl. No.: 15/236,191

(22) Filed: Aug. 12, 2016

(65) Prior Publication Data

US 2017/0045484 A1 Feb. 16, 2017

(30) Foreign Application Priority Data

Aug. 12, 2015 (KR) ........................ 10-2015-0113721

(51) Int. Cl.

| | |
|---|---|
| ***G01N 31/22*** | (2006.01) |
| ***G01N 33/00*** | (2006.01) |
| ***C07C 229/14*** | (2006.01) |
| ***C07C 271/02*** | (2006.01) |
| ***C07C 309/51*** | (2006.01) |

(52) U.S. Cl.

CPC ......... *G01N 33/004* (2013.01); *C07C 229/14* (2013.01); *C07C 271/02* (2013.01); *C07C 309/51* (2013.01); *G01N 31/223* (2013.01); *C07C 2601/16* (2017.05); *C07C 2603/24* (2017.05)

(58) Field of Classification Search

None

See application file for complete search history.

(56) References Cited

U.S. PATENT DOCUMENTS

| | | | | |
|---|---|---|---|---|
| 4,405,586 A * | 9/1983 | Sartori | B01D 53/1493 174/DIG. 22 |
| 2015/0165375 A1* | 6/2015 | Fischer | B01D 53/1475 423/225 |

OTHER PUBLICATIONS

Billing, J. et al. “Amphiphilic Anthracene-Amino Acid Conjugates as Simple Carbohydrate Receptors in Water,” J. Supramolecular Chemistry, vol. 14, Issue: 4, pp. 367-372 (Year: 2002).*

SciFinder abstract of Billing, J. et al. “Amphiphilic Anthracene-Amino Acid Conjugates as Simple Carbohydrate Receptors in Water,” J. Supramolecular Chemistry, vol. 14, Issue: 4, pp. 367-372 (Year: 2002).*

(Continued)

*Primary Examiner* — Christopher Adam Hixson

*Assistant Examiner* — Michelle Adams

(74) *Attorney, Agent, or Firm* — Hauptman Ham, LLP

(57) ABSTRACT

The present invention relates to an amino acid-based compound for detecting carbon dioxide, and to a carbon dioxide chemical sensor and a carbon dioxide detection method using the compound, wherein the compound having selectivity with respect to carbon dioxide exhibits a high selectivity to carbon dioxide and thus may detect carbon dioxide of a very low concentration, exhibits excellent light-absorbing or fluorescent characteristics, and, in particular, may achieve an effect of detecting carbon dioxide in real time.

7 Claims, 30 Drawing Sheets

(56) References Cited

OTHER PUBLICATIONS

Kang, S. et al. "Intra-molecular hydrogen bonding stabilization based-fluorescent chemosensor for CO2: Application to screen relative activities of CO2 absorbents," Dyes and Pigments, vol. 123, Dec. 2015, pp. 125-131; Available online Aug. 4, 2015. (Year: 2015).*
Liu, A.-H. et al. "Equimolar CO2 Capture by N-Substituted Amino Acid Salts and Subsequent Conversion," Angew. Chem. Int. Ed. 2012, 51, 11306-11310 (Year: 2012).*
Royce N. Dansby-Sparks et al., "Fluorescent-Dye-Doped Sol-Gel Sensor for Highly Sensitive Carbon Dioxide Gas Detection below Atmospheric Concentrations", Analytical Chemistry, vol. 82, No. 2, Jan. 15, 2010, p. 593-600.
Yang Liu et al., "Fluorescent Chemosensor for Detection and Quantitation of Carbon Dioxide Gas", J. American Chemical Society 2010, vol. 132, No. 40, p. 13951-13953.
Seungyoon Kang et al., "Intra-molecular hydrogen bonding stabilization based-fluorescent chemosensor for CO2: application to screen relative activities of CO2 absorbents", Dyes and Pigments, Published on Jul. 25, 2015, Total pp. 53.
Seungyoon Kang et al, "Development of CO2 absorbent screening method based on fluorescent chemosensor for CO2" with English translation of Abstract, Master thesis of Chung-Ang University, Published on Feb. 5, 2015 , Total pp. 63.

* cited by examiner

| | | | |
|---|---|---|---|
| Equation | y = a+b*x | | |
| Weight | No Weighting | | |
| Residual Sum of Squares | 0.02022 | | |
| Pearson's r | 0.99913 | | |
| Adj. R-Square | 0.99797 | | |
| | | Valve | Standeard Error |
| B | Intercept | 29.34521 | 0.43396 |
| B | Slope | 4.21029 | 0.07183 |

1 2 3

CARBON DIOXIDE CHEMICAL SENSOR HAVING AMINO ACID-BASED COMPOUND AND CARBON DIOXIDE DETECTION METHOD USING THE SAME

CROSS REFERENCE TO RELATED APPLICATIONS

This application is based upon and claims the benefit of priority from Korean Patent Application No. 10-2015-0113721, filed on Aug. 12, 2015 in the Korean Intellectual Property Office, the entire contents of which are incorporated herein by reference.

BACKGROUND

1. Technical Field

The present invention relates to an amino acid-based compound for detecting carbon dioxide, and to a carbon dioxide chemical sensor and a carbon dioxide detection method using the amino acid-based compound.

2. Description of the Related Art

Carbon dioxide in the atmosphere is a chemically stable gas in the air and is a main factor that causes global warming. In this regard, a need of controlling carbon dioxide concentration in various fields such as for in-door air conditioning in the building and in a greenhouse for gardening has increased, as well as a need to resolve environmental problems.

Currently, as a method for measuring a carbon dioxide concentration, an optical method (a NDIR method) has been most frequently used, but the method uses a principle of carbon dioxide absorbing infrared light of a particular wavelength, and thus the measurement requires a sealed space, and the elements used in the measurement are large in volume and heavy.

Further, some elements that constitute such an apparatus are expensive and require complicated configuration for control, and thus the method may not be applied widely.

On the other hand, since a recently developed carbon dioxide chemical sensor is convenient and has high sensitivity of fluorescence, compared to those of other conventional detection methods, attention has been drawn to the carbon dioxide chemical sensor, and thus compounds having various structures have been reported.

One example is a carbon dioxide chemical sensor that is synthesized by bonding a pH indicator and a compound capable of absorbing carbon dioxide, which measures pH change of water to weak acid before and after absorbing carbon dioxide due to carbonate ions ($HCO_3^-$) that are produced when carbon dioxide is hydrated while being dissolved in water. However, when disruption occurs by factors pH other than carbon dioxide that may influence pH and when the indicator has a low solubility to water, an additional agent is needed, and thus accuracy of the measurement is significantly low.

Also, another example is a carbon dioxide sensor using a compound having an aggregation induced emission (ME) phenomenon and an amine aqueous solution. When the amine aqueous solution is bubbled with carbon dioxide, carbonate ionic liquid is formed, and thus carbon dioxide may be detected by using AIE dyes such as hexaphenylsilole (HPS) or tetraphenylethylene (TPE) which may have the optical property change due to polarity and viscosity of the system. However, the sensor is only useful in detection of carbon dioxide at a high concentration, and the carbon dioxide sensor may not have a high sensitivity. Also, accuracy of the sensor deteriorates due to a high volatility of the amine aqueous solution.

The carbon dioxide chemical sensors described above are limited in detection since they essentially need water or additional auxiliary factors to operate the system. Such limitation restricted the use of the sensor to carbon dioxide detection in various processes as well as the use of the sensor in daily life, and the sensor is not suitable to be used for analysis of activity of a carbon dioxide adsorbent.

Also, fluorescence of the carbon dioxide sensors is not renatured once the sensors are exposed to carbon dioxide, and thus the carbon dioxide sensors cannot be re-used.

SUMMARY

It is an aspect of the present invention to provide a novel compound having a selectivity to carbon dioxide, which exhibits a high selectivity to carbon dioxide, is capable of detecting carbon dioxide of a very low concentration, exhibits excellent light-absorbing or fluorescent characteristics, and, in particular, may detect carbon dioxide in real time.

It is another aspect of the present invention to provide a novel compound which bonds to carbon dioxide and exhibits excellent light-absorbing or fluorescent characteristics.

It is another aspect of the present invention to provide a carbon dioxide sensor using the compound.

It is another aspect of the present invention to provide a carbon dioxide detection method that is selective to carbon dioxide only and has excellent sensitivity by including contacting the carbon dioxide sensor with carbon dioxide.

It is another aspect of the present invention to provide a method of detecting carbon dioxide, separating the carbon dioxide from the carbon dioxide sensor to re-use the carbon dioxide sensor.

It is another aspect of the present invention to provide a carbon dioxide sensor of a type that is on or off based on a predetermined carbon dioxide concentration.

It is another aspect of the present invention to provide various applications using the carbon dioxide sensor.

The present invention is not limited to the above aspect and other aspects of the present invention will be clearly understood by those skilled in the art from the following description.

In accordance with one aspect of the present invention, a compound represented by Formula 1 is provided:

[Formula 1]

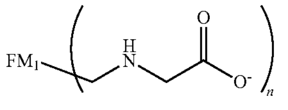

wherein, in Formula 1, $FM_1$ is any one selected from compounds represented by Structural Formula 1, and n is a real number of 1 to 2:

[Structural Formula 1]

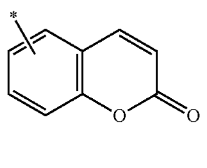

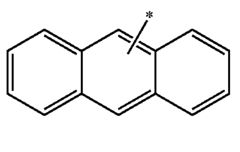

-continued

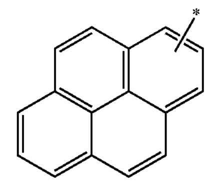

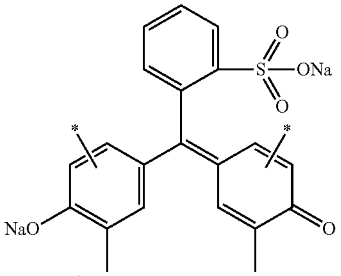

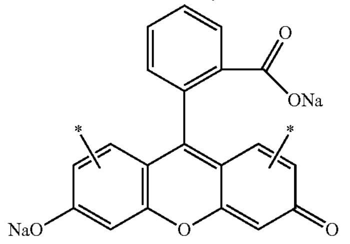

In Formula 1, when n is 1, $FM_1$ may be any one selected from the group consisting of

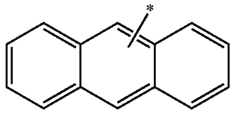
,
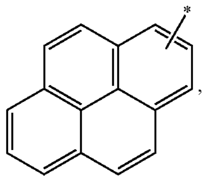
, and
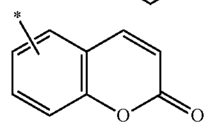

among the compounds represented by Structural Formula 1.

In Formula 1, when n is 2, $FM_1$ may be

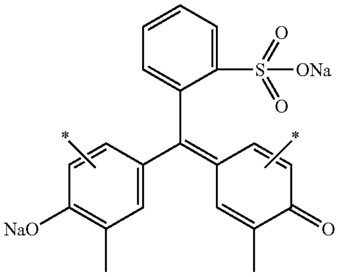
or
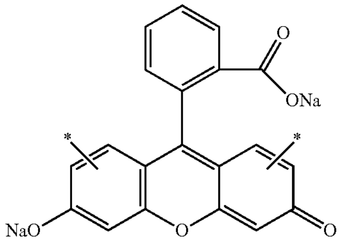

among the compounds represented by Structural Formula 1.

The compound represented by Formula 1 may be a compound represented by Formula 2 or Formula 3:

[Formula 2]

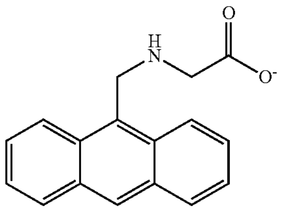

[Formula 3]

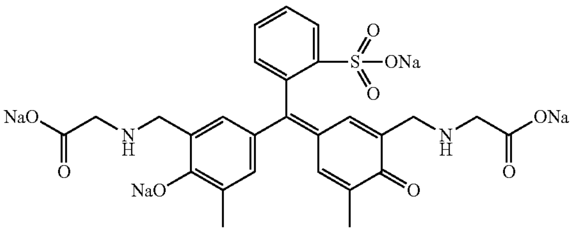

In accordance with another aspect of the present invention, a compound represented by Formula 4 is provided:

[Formula 4]

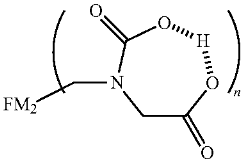

wherein, in Formula 4, $FM_2$ is any one selected from compounds represented by Structural Formula 2, and n is a real number of 1 to 2:

[Structural Formula 2]

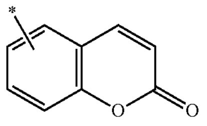

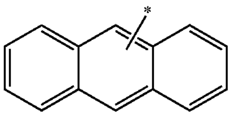

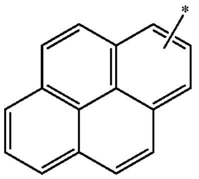

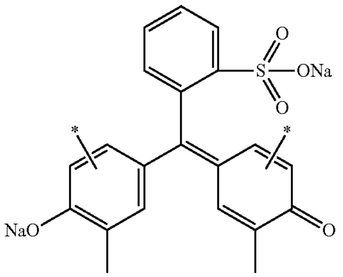

-continued

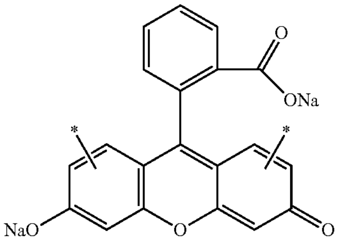

In Formula 4, when n is 1, $FM_2$ may be one selected from the group consisting of

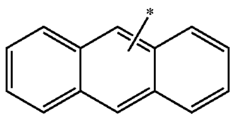,

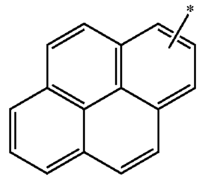, and

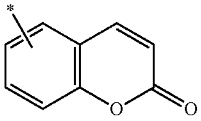

among the compounds represented by Structural Formula 2.

In Formula 4, when n is 2, $FM_2$ may be

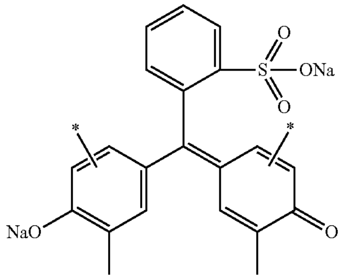

or

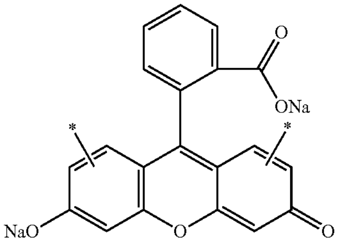

among the compounds of Structural Formula 2.

The compound represented by Formula 4 may be a compound represented by Formula 5 or Formula 6:

[Formula 5]

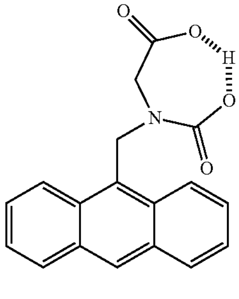

-continued

[Formula 6]

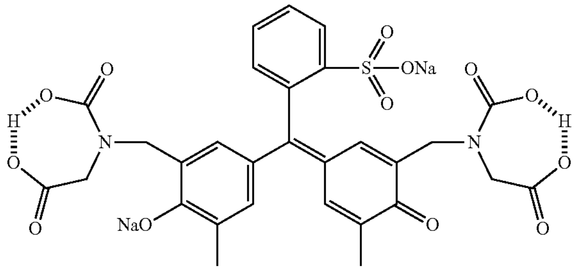

In accordance with another aspect of the present invention, a carbon dioxide sensor including the compound represented by Formula 1 is provided.

The carbon dioxide sensor may have fluorescence change within a range of 400 nm to 450 nm or light-absorptivity change in a light-absorption band within a range of 400 nm to 450 nm and a light-absorption band within a range of 550 nm to 600 nm or may exhibit color change, after detecting carbon dioxide.

A detection limit of the carbon dioxide sensor may be 2.04 ppm.

In accordance with another aspect of the present invention, a method of detecting carbon dioxide is provided, wherein the method includes:

I) exposing a carbon dioxide sensor comprising the compound represented by Formula 1 in a sample including carbon dioxide;

II) allowing the carbon dioxide sensor and carbon dioxide in the sample to react through the exposing in step I) to form the compound represented by Formula 4; and III) measuring light-absorptivity or fluorescence change of the compound represented by Formula 4 formed in step II).

In accordance with another aspect of the present invention, a method of regenerating a carbon dioxide sensor is provided, wherein the method includes:

I) detecting carbon dioxide by converting the compound represented by Formula 1 to the compound represented by Formula 4 by allowing the compound represented by Formula 1 to react with carbon dioxide; and II) converting the compound represented by Formula 4 to the compound represented by Formula 1 by separating carbon dioxide from the compound represented by Formula 4.

In step II), nitrogen may be injected to convert the compound represented by Formula 4 to the compound represented by Formula 1 by separating carbon dioxide from the compound represented by Formula 4.

In step II), 100 to 200 ml of nitrogen may be injected based on 50 μM of the compound represented by Formula 4.

In accordance with another aspect of the present invention, a carbon dioxide sensor of an on/off type is provided, wherein the carbon dioxide sensor includes (i) a carbon dioxide adsorbent material free of a chromophore; and (ii) a compound represented by Formula 1.

The (i) carbon dioxide adsorbent material free of a chromophore may be any one selected from triethanolamine (TEA), N-methyldiethanolamine (MDEA), dimethylethanmolamine (DMEA), diethanolamine (DEA), N-methylethanolamine (MMEA), monoethanolamine (MEA), and 2-piperidinemethanol (PM).

A carbon dioxide affinity of the (i) carbon dioxide adsorbent material free of a chromophore may be higher than a carbon dioxide affinity of the (ii) compound represented by Formula 1.

In accordance with another aspect of the present invention, a kimchi ripening degree detection device, an alcohol and carbon dioxide detection sensor, or a kimchi ripening degree refrigerator may each include the carbon dioxide sensor.

Effect of Invention

According to one or more embodiments of the present invention, a compound having a selectivity to carbon dioxide may exhibit a high selectivity to carbon dioxide, is capable of detecting carbon dioxide at a very low concentration, exhibits excellent light-absorbing or fluorescent characteristics, and, in particular, may achieve an effect of detecting carbon dioxide in real time.

In addition, no separate additive is required, that thus there is no limit on various application of the compound.

DETAILED DESCRIPTION

Figure 1:
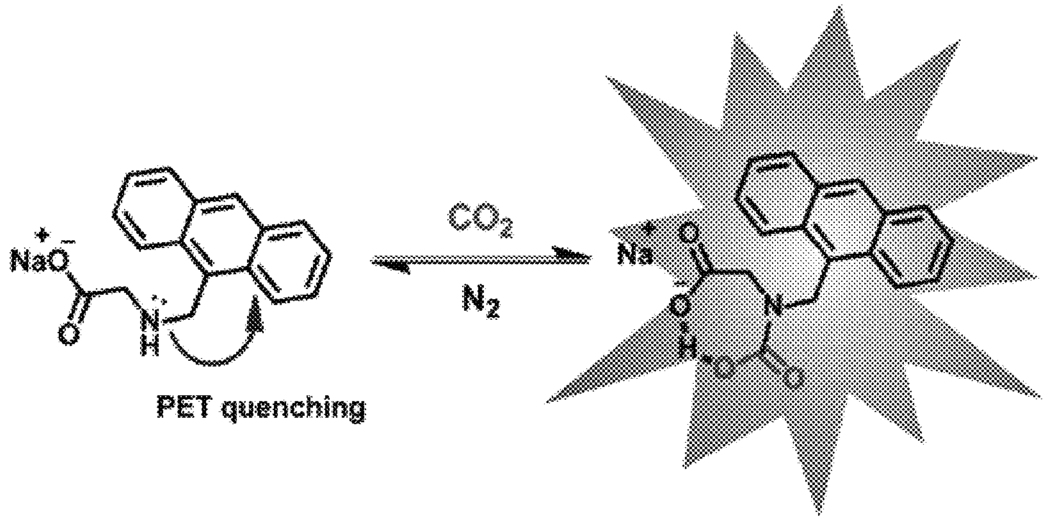
FIG. 1 is a conceptive view that illustrates a structure of a compound represented by Formula 2, and a process of preparing a compound represented by Formula 5 from the compound represented by Formula 2 and structures of the compounds, according to the present invention.

Hereinafter, embodiments of the present invention will be described in detail with reference to the accompanying drawings. It should be understood that the present invention is not limited to the following embodiments, and that the embodiments are provided for illustrative purposes only. The scope of the invention should be defined only by the accompanying claims and equivalents thereof.

Hereinafter, various aspects and embodiments of the present invention will be described in detail.

Conventional chemical sensors for detecting carbon dioxide that have been studied up to date mostly operate when $F^-$ or triethylamine (TEA) is present as an additive in the sensor system or confirm a pH change based on an indicator in an aqueous solution.

The carbon dioxide chemical sensors have low accuracy, may not detect carbon dioxide at a low concentration, and have a significantly low sensitivity. Moreover, due to characteristics such as additional agents and volatility, the sensors had restrictions in terms of its application in various areas of real-life situation.

Therefore, the present invention has focused on developing a chemical sensor of a "turn-on" type that may resolve the problems and limitations described above and may selectively detect only carbon dioxide at an excellent sensitivity even when no other additives is present, thereby completing the present invention.

One aspect of the present invention is to provide a compound represented by Formula 1:

[Formula 1]

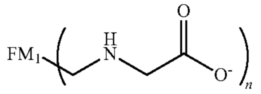

In Formula 1, $FM_1$ is one selected from compounds represented by Structural Formula 1, and n is a real number of 1 to 2:

[Structural Formula 1]

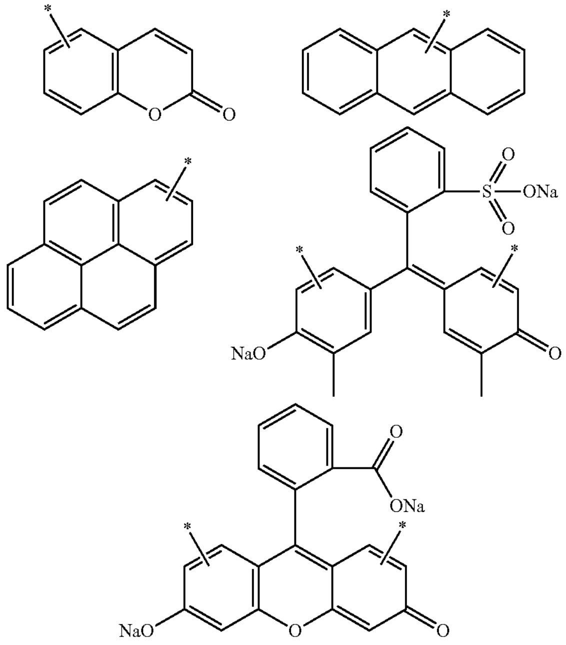

The compound represented by Formula 1 is a compound in the state of "turn-off" before reacting with carbon dioxide.

In particular, the compound represented by Formula 1 may be formed as a compound in the state of "turn-on" which occurs by light-absorbance or intensive exhibition of fluorescence according to the reaction pathway with carbon dioxide. First, a chromophore formed of two or more benzene rings in the compound represented by Formula 1 may extinct fluorescence of the chromophore due to photo-induced electron transfer (PET), but when the compound reacts with carbon dioxide, the PET phenomenon is blocked, which allows the compound to exhibit "turn-on" characteristics that intensively show native fluorescence of the chromophore.

Alternatively, the compound represented by Formula 1 may have a structure that does not absorb light, but when the compound reacts with carbon dioxide, the structure of the compound itself may change to a structure having light-absorbance, that is, color change (see FIG. 2), and thus the compound may exhibit "turn-on" characteristics.

Also, when a functional group other than $-(CH_2NHCH_2COO^-)_n$, is present in Formula 1, as it will be described in examples, the compound may not have a stabilized structure, in which a intramolecular hydrogen bond with carbon oxide is formed, and thus light-absorbance or fluorescence exhibition of the compound does not change due to the presence of carbon dioxide or a volume difference, which disables detection of carbon dioxide.

Preferably, in Formula 1, when n is 1, $FM_1$ may be any one selected from the group consisting of

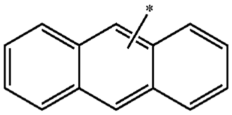
,
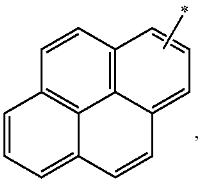
, and
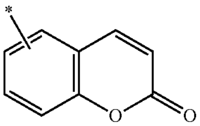

from Structural Formula 1.

In Formula 1, when n is 2, $FM_1$ may be

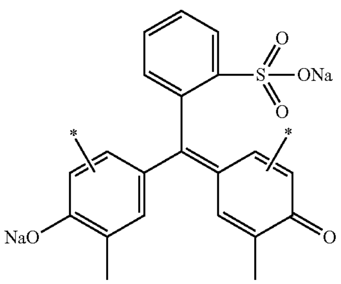
or
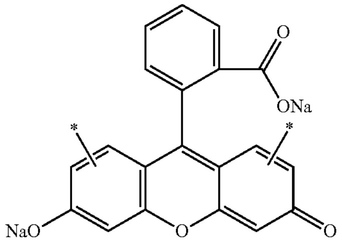

from Structural Formula 1.

More preferably, the compound represented by Formula 1 may be a compound represented by Formula 2 or Formula 3:

[Formula 2]

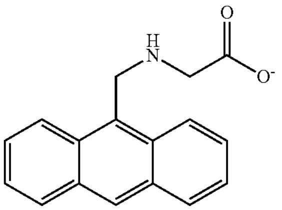

[Formula 3]

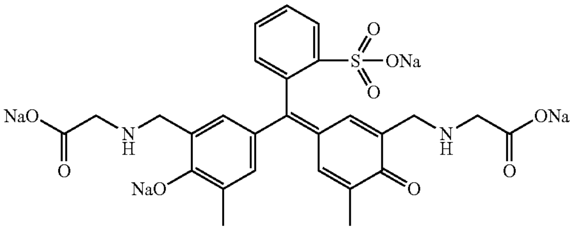

As shown in FIG. 1, the compound represented by Formula 2 is characterized in that fluorescence is weakly exhibited due to PET quenching by an unshared electron pair of a nitrogen atom located at a benzylic position of anthracene.

Figure 2:
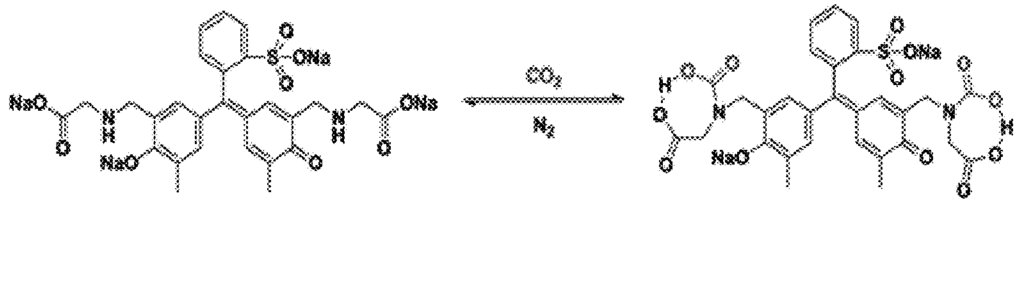
FIG. 2 is a conceptive view that illustrates a structure of compound represented by Formula 3, and a process of preparing a compound represented by Formula 6 from the compound represented by Formula 3 and structures of the compounds, according to the present invention.

Also, as shown in FIG. 2, the compound represented by Formula 3 includes three benzene rings and exhibits the maximum and the minimum light-absorbance within a native light-absorption band, and, in particular, a ratio ($A_{440}/A_{583}$) of a light-absorption band at 440 nm ($A_{440}$) and a light-absorption band at 583 nm ($A_{583}$) is between 1 to 1.5. Here, the color is observed red.

That is, when a ratio ($A_{440}/A_{583}$) of a light-absorption band at 440 nm ($A_{440}$) and a light-absorption band at 583 nm ($A_{583}$) is between 1 to 1.5 or the color is observed red, it may be known that the compound represented by Formula 1, or, preferably, the compound represented by Formula 3 is at the state before reacting with carbon dioxide.

Also, as it will be described in examples, a detection limit of carbon dioxide of the compound represented by Formula 1, preferably, the compound represented by Formula 2 or Formula 3, or, more preferably, the compound represented by Formula 2 is as low as 1 to 2.1 ppm, or, preferably, 2.04 ppm.

In this regard, the compound represented by Formula 1, preferably, the compound represented by Formula 2 or Formula 3, or, more preferably, the compound represented by Formula 2 is has a sensitivity 10 times or greater than that of a conventional carbon dioxide fluorescent chemical sensor.

According to another aspect of the present invention, provided is a compound represented by Formula 4:

[Formula 4]

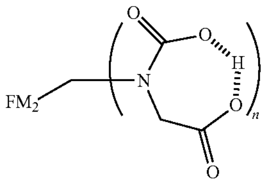

In Formula 4, $FM_2$ is any one selected from compounds represented by Structural Formula 2, and n is a real number of 1 to 2:

[Structural Formula 2]

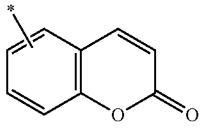
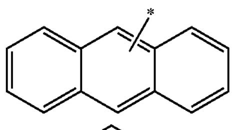
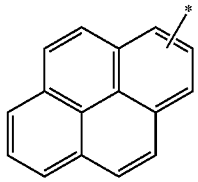
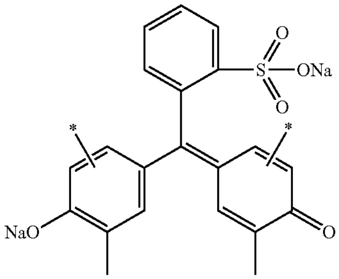

-continued

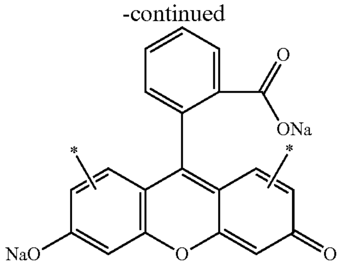

The compound represented by Formula 4 is a compound in the state of "turn-on" that exhibits native light-absorbance or intensive fluorescence which occurs when the compound represented by Formula 1 reacts with carbon dioxide.

In particular, the compound represented by Formula 4 may exhibit light-absorbance or intensive fluorescence according to the reaction pathway with carbon dioxide. First, when the compound represented by Formula 1 reacts with carbon dioxide, quenching generated by PET does not occur, and thus the compound represented by Formula 4 may be in the "turn-on" state at which the native fluorescence of $FM_2$ is intensively exhibited.

Alternatively, when the compound represented by Formula 1 reacts with carbon dioxide, a structure of the compound represented by Formula 1 changes to a structure of the compound represented by Formula 4, and thus the compound represented by Formula 4 may be in the "turn-on" state, at which the native light-absorbance of the compound represented by Formula 4 is intensively exhibited.

Here, when the compound represented by Formula 1 reacts with carbon dioxide, a carboxylate group adjacent to unstable carbamic acid stabilizes the compound by an intramolecular hydrogen bond without an additional additive, which allows formation of the compound represented by Formula 4 in the state of "turn-on" that intensively exhibits the native light-absorbance or fluorescent light of the compound represented by Formula 4, and thus the light-absorbance or fluorescent light may be measured to qualitatively or quantitatively detect carbon dioxide.

The compound represented by Formula 4 may be used as a chemical sensor in the form of "turn-on" having a good sensitivity.

Also, the compound represented by Formula 4 may be re-used as the compound represented by Formula 1 by separating carbon dioxide bound to the compound represented by Formula 4 through nitrogen injection.

Here, an amount of the injected nitrogen may be 50 to 200 ml, or, preferably, 100 to 200 ml, based on 50 μM of the compound represented by Formula 4.

Preferably, in Formula 4, when n is 1, $FM_2$ may be any one selected from the group consisting of

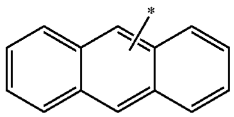 , 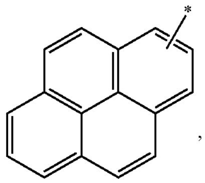 , and

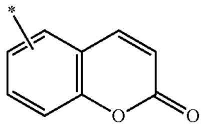

from Structural Formula 2.

Also, in Formula 4, when n is 1, $FM_2$ may be

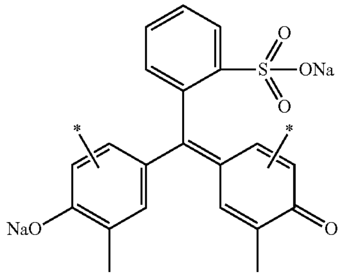 or

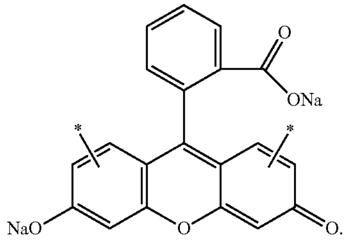.

More preferably, the compound represented by Formula 4 may be a compound represented by Formula 5 or Formula 6:

[Formula 5]

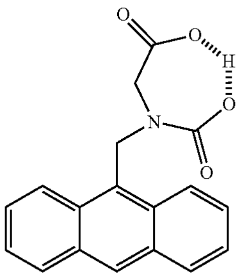

[Formula 6]

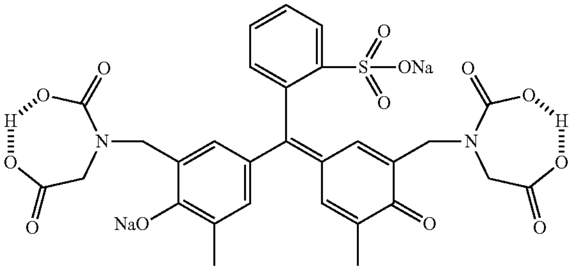

As shown in FIG. 1, the compound represented by Formula 5 in the state of "turn-on" may be formed through reaction with carbon dioxide, in which a carboxylate group adjacent to unstable carbamic acid stabilizes the compound by an intramolecular hydrogen bond without an additional additive.

That is, as the unshared electron pair of a nitrogen atom located at a benzylic position of anthracene is stabilized, the quenching does not occur, and thus the native fluorescence of anthracene may be emitted, which may be then detected within 400 to 450 nm of a fluorescent intensity, and thus the presence of carbon dioxide may be qualitatively or quantitatively detected.

Also, as shown in FIG. 2, the compound represented by Formula 6 is a trityl derivative including three benzene rings, and when the compound represented by Formula 6 reacts with the injected carbon dioxide, a carboxylate group adjacent to unstable carbamic acid stabilizes the compound by an intramolecular hydrogen bond, and thus the compound represented by Formula 3 may be changed into the compound represented by Formula 6 which has the native light-absorbance, that is, having a particular color, and "turn-on" characteristics.

Here, the compound represented by Formula 6 is observed yellow, and this denotes an effective color change from the compound represented by Formula 3 observed in red to the compound represented by Formula 6 observed in yellow through the reaction with carbon dioxide.

That is, in this regard, since a color change due to an increase in a light-absorption band of 400 to 450 nm and a decrease in a light-absorption band of 550 to 600 nm of the trityl derivative may be measured and observed, the presence of carbon dioxide may be qualitatively or quantitatively detected.

The compound represented by Formula 4 may have a fluorescence change within 400 to 450 nm, a light-absorbance change within a light-absorption band of 400 to 450 nm and a light-absorption band of 550 to 600 nm, or a color change, where the color change, light-absorbance, and fluorescence intensity of the compound represented by Formula 4 that is formed by bonding with carbon dioxide may be measured, and thus the presence of carbon dioxide may be qualitatively or quantitatively measured through the changes on the compound before and after binding with carbon dioxide.

Also, another aspect of the present invention provides a carbon dioxide sensor including the compound represented by Formula 1.

As shown in FIG. 1, the compound represented by Formula 1 the native fluorescence of the compound may be shown at a weak intensity or may not be shown due to quenching by an unshared electron pair of a nitrogen atom located at a benzylic position, but when the compound represented by Formula 1 reacts with carbon dioxide, a carboxylate group adjacent to unstable carbamic acid stabilizes the compound by an intramolecular hydrogen bond, which forms the compound represented by Formula 4, and thus excellent fluorescent characteristics may be exhibited. In particular, a feature of exhibiting further excellent fluorescence change according to an increase in a concentration of carbon dioxide may be used to quantitatively or qualitatively detect carbon dioxide.

Also, the compound represented by Formula 1 has the maximum and minimum light-absorption ratios within the native light-absorption band, but when the compound represented by Formula 1 reacts with carbon oxide, a carboxylate group adjacent to unstable carbamic acid stabilizes the compound by an intramolecular hydrogen bond, and thus the compound represented by Formula 1 is changed into the compound represented by Formula 4 that has the maximum and minimum light-absorption ratios within the native light-absorption band. Particularly, a feature of a light-absorption change, where the difference between the maximum and minimum light-absorption ratios of the compound represented by Formula 1 and the maximum and minimum light-absorption ratios of the compound represented by Formula 4 increases as a carbon dioxide concentration increases, may be used to qualitatively or quantitatively detect carbon dioxide.

That is, the carbon dioxide sensor has light-absorption and fluorescence change according to a concentration of carbon dioxide. Since the carbon dioxide concentration increases, better light-absorption and fluorescence change may be exhibited, this feature may be used to qualitatively or quantitatively detect carbon dioxide.

Further, the compound represented by Formula 1 may have excellent reactivity with respect to carbon dioxide only.

Also, the compound represented by Formula 4, i.e., the carbon dioxide sensor, may be renatured to the compound represented by Formula 1 by nitrogen injection and bubbling and thus may be re-used through a simple nitrogen supplying process.

Also, the carbon dioxide sensor exhibits light-absorption and fluorescence change of the compound through the change of the intramolecular hydrogen bond due to detection of carbon dioxide, and since a weight loss of the compound represented by Formula 1 included in the carbon dioxide sensor is very small and light-absorption and fluorescent intensity do not decrease, the compound represented by Formula 1 may be re-used 100 times or more or, preferably, 5 times or more.

Also, when the carbon dioxide sensor of the present invention is used, carbon dioxide may be detected in all an aqueous solution phase, an organic solution phase, or a mixture phase of an organic solution and an aqueous solution.

Also, a detection limit of the carbon dioxide sensor is as excellent as 2.04 ppm.

Figure 27:
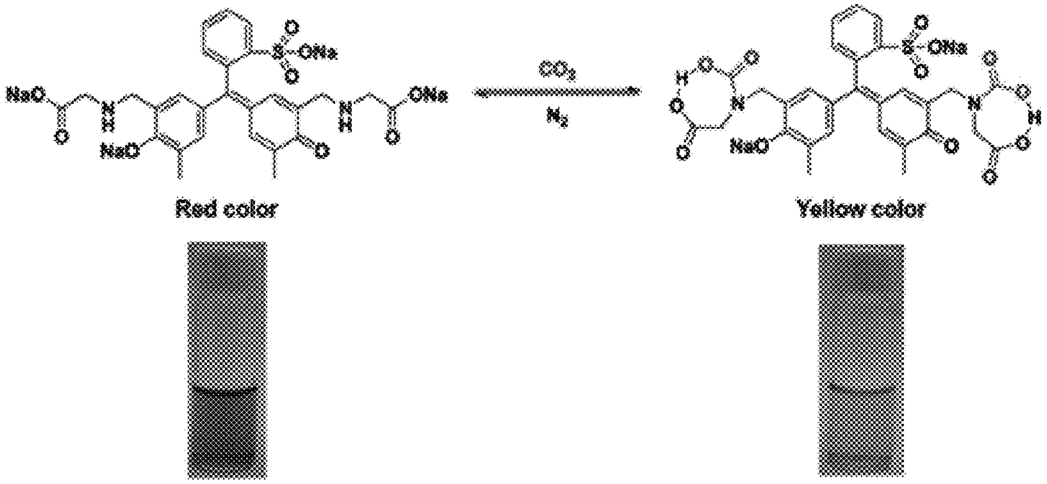
FIG. 27 is an image that shows color change of a solution prepared by bubbling a solution of a compound (Formula 3) synthesized in Preparation Example 2 with carbon dioxide.

In particular, the carbon dioxide sensor may exhibit red in the case of the compound represented by Formula 3, may exhibit yellow after the detection of carbon dioxide, and may be renatured to red after separating carbon dioxide (FIG. 27).

Therefore, since the carbon dioxide sensor including the compound represented by Formula 1 selectively reacts with carbon dioxide without an additional additive or an auxiliary factor, exhibits light-absorption and fluorescence change according to the reaction with carbon dioxide due to excellent fluorescence, and has a sensitivity 10 times or greater than that of the conventional dioxide fluorescence chemical sensor, the compound represented by Formula 1 may be effectively used as a sensor for detecting carbon dioxide.

Also, another aspect of the present invention provides a method of detecting carbon dioxide.

The method of detecting carbon dioxide includes:

I) exposing a carbon dioxide sensor comprising the compound represented by Formula 1 in a sample comprising carbon dioxide;

II) allowing the carbon dioxide sensor and carbon dioxide in the sample to react through the exposing in step I) to form the compound of represented by Formula 4; and III) measuring light-absorptivity or fluorescence change of the compound represented by Formula 4 formed in step II).

Here, the method of detecting carbon dioxide may qualitatively or quantitatively measure carbon dioxide from the light-absorptivity or fluorescence change.

The fluorescence change may be may be easily detected by measuring and observing the change within a range of 400 to 450 nm.

Also, the light-absorptivity change may be easily detected by measuring the change within a light-absorption band in a range of 400 to 450 nm and a light-absorption band in a range of 550 to 600 nm, where, preferably, the change may be measured by a ratio ($A_{440}/A_{583}$) of a light-absorption band at 440 nm ($A_{440}$) and a light-absorption band at 583 nm ($A_{583}$).

A degree of the light-absorptivity or fluorescence change may vary depending on a carbon dioxide concentration in the sample, and thus the presence of carbon dioxide in the sample may be qualitatively or quantitatively analyzed.

The sample may be any material that is obtained from the body or environment which requires detection of the presence of carbon dioxide. For example, the sample may be water obtained from river or sea to evaluate environmental contamination or may be body fluid or blood of an animal or a human.

Also, when the carbon dioxide sensor of the present invention is used, carbon dioxide may be detected in all an aqueous solution phase, an organic solution phase, or a mixture phase of an organic solution and an aqueous solution.

Another aspect of the present invention provides a method of regenerating a carbon dioxide sensor, and the method includes:

I) detecting carbon dioxide by converting the compound represented by Formula 1 to the compound represented by Formula 4 by allowing the compound represented by Formula 1 to react with carbon dioxide; and II) converting the compound represented by Formula 4 to the compound represented by Formula 1 by separating carbon dioxide from the compound represented by Formula 4.

In step II), it is preferable that nitrogen is injected to separate carbon dioxide from the compound represented by Formula 4.

In step II), it is preferable that an amount of the nitrogen being injected based on 50 μM of the compound represented by Formula 4 may be 100 ml or more, or, preferably, 100 to 200 ml.

Here, when the amount of the nitrogen is less than 100 ml based on 50 μM of the compound represented by Formula 4, carbon dioxide is not completely separated from the compound represented by Formula 4, and thus the amount of the nitrogen is not particularly limited thereto as long as the amount is 100 ml or more based on 50 μM of the compound represented by Formula 4 in step II).

However, when the nitrogen is injected at an amount greater than 200 ml based on 50 μM of the compound represented by Formula 4, unnecessary cost and time need to be added, and thus it is not economical.

Another aspect of the present invention provides a carbon dioxide sensor of an on/off type, wherein the carbon dioxide sensor includes: (i) a carbon dioxide adsorbent material free of a chromophore; and (ii) a compound represented by Formula 1.

Since the carbon dioxide sensor of an on/off type may further include (i) a carbon dioxide adsorbent material that is free of a chromophore and has a carbon dioxide affinity higher than that of the (ii) compound represented by Formula 1, the (i) carbon dioxide adsorbent material free of a chromophore first adsorbs carbon dioxide, and then the (ii) compound represented by Formula 1 reacts with carbon dioxide, which results in light-absorption or fluorescence change.

That is, when a carbon dioxide concentration in the sample to be measured is higher than a carbon dioxide concentration that may be adsorbed by the (i) carbon dioxide adsorbent material free of a chromophore, the sensor may operate as a carbon dioxide sensor of an off/on type that emits fluorescence.

In other words, when the carbon dioxide concentration in the sample is lower than a carbon dioxide concentration that may be adsorbed by the (i) carbon dioxide adsorbent material free of a chromophore (also, referred to as 'a set carbon dioxide concentration'), the (i) carbon dioxide adsorbent material free of a chromophore is first adsorbed, and thus light-absorption or fluorescence change may not occur. When the carbon dioxide concentration in the sample is higher than the set carbon dioxide concentration and is beyond the adsorption range of the (i) carbon dioxide adsorbent material free of a chromophore, light-absorption or fluorescence change may occur due to the (ii) compound represented by Formula 1, and thus the sensor may be effectively used as an off/on-type carbon dioxide sensor.

The (i) carbon dioxide adsorbent material free of a chromophore may be any material having a carbon dioxide affinity higher than that of the (ii) compound represented by Formula 1, and examples of the material may be, but not limited to, any one selected from triethanolamine (TEA), N-methyldiethanolamine (MDEA), dimethylethanmolamine (DMEA), diethanolamine (DEA), N-methylethanolamine (MMEA), monoethanolamine (MEA), and 2-piperidinemethanol (PM). The (i) carbon dioxide adsorbent material free of a chromophore may be, preferably, PM, MEA, or MMEA, which have the most excellent absorption capacity with respect to carbon dioxide.

A carbon dioxide affinity of the (i) carbon dioxide adsorbent material free of a chromophore may be higher than a carbon dioxide affinity of the (ii) compound represented by Formula 1, but when a carbon dioxide affinity of the (i) carbon dioxide adsorbent material free of a chromophore is lower than a carbon dioxide affinity of the (ii) compound represented by Formula 1, carbon dioxide may first react with the (ii) compound represented by Formula 1 despite a carbon dioxide concentration in the sample is lower than the set carbon dioxide concentration, and thus light-absorption or fluorescence change may occur.

The carbon dioxide affinity of the carbon dioxide adsorbent material free of a chromophore, described above, may be preferable when absorption capacity×initial adsorption rate measured by using the compound represented by Formula 1 according to the present invention is 0.007 or higher, or, more preferably, in a range of 0.0076 or higher to 0.02 or lower.

When the carbon dioxide affinity of the carbon dioxide adsorbent material free of a chromophore calculated by absorption capacity x initial adsorption rate as measured by using the compound represented by Formula 1 according to the present invention is lower than 0.007, the reaction with carbon dioxide occurs slower than that of the compound represented by Formula 1 according to the present invention, and thus light-absorption or fluorescence change may occur despite a carbon dioxide concentration in the sample is lower than the set carbon dioxide concentration.

[Formula 1]

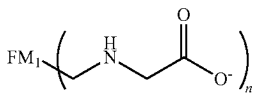

In Formula 1, $FM_1$ is any one selected from compounds represented by Structural Formula 1, and n is a real number of 1 to 2:

[Structural Formula 1]

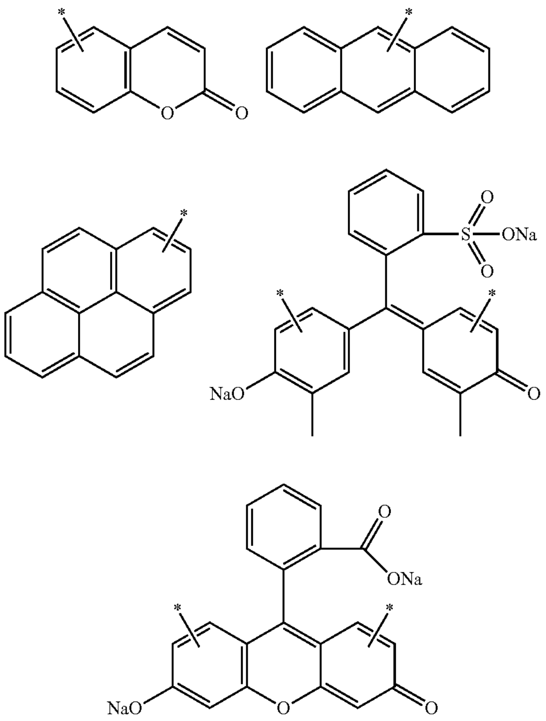

In Formula 1, when n is 1, $FM_1$ may be any one selected from the group consisting of

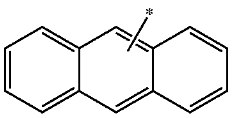,

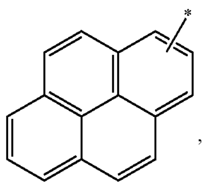, and

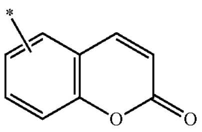

among the compounds represented by Structural Formula 1.

In Formula 1, when n is 2, $FM_1$ may be

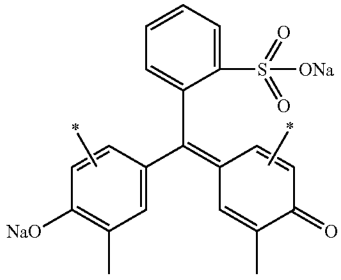

or

-continued

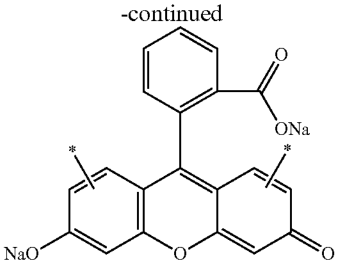

among the compounds represented by Structural Formula 1.

More preferably, the compound represented by Formula 1 may be a compound represented by Formula 2 or Formula 3:

[Formula 2]

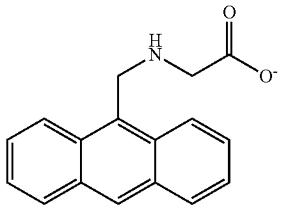

[Formula 3]

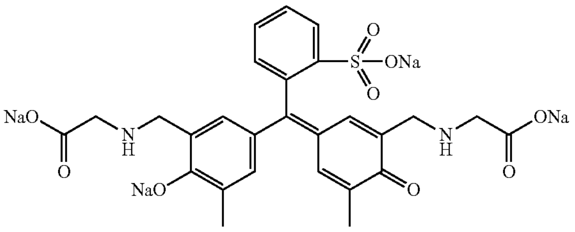

The carbon dioxide sensor of various types described above may detect a carbon dioxide concentration that may influence fermentation of kimchi, and thus such feature may be applied to various uses including a kimchi ripening degree detection device, an alcohol and carbon dioxide detection sensor, or a kimchi ripening degree refrigerator.

Hereinafter, the present invention will be described in detail by referring to examples, but the scope and embodiments of the present invention should not be construed as reduced or limited to the examples set forth herein. Also, it will be apparent to those of skill in the art that the present disclosure may be practiced without such specific details, and such modification and changes belong to the scope of the discloser, which is defined in the following claims.

Also, the experiment results set forth herein only provides representative experiment results of Examples and Comparative Examples, and the effects of various embodiments of the present invention that are not provided hereinafter will be described in the corresponding part of the present specification.

Example 1. Synthesis of Compound Represented by Formula 1

[Reaction scheme 1]

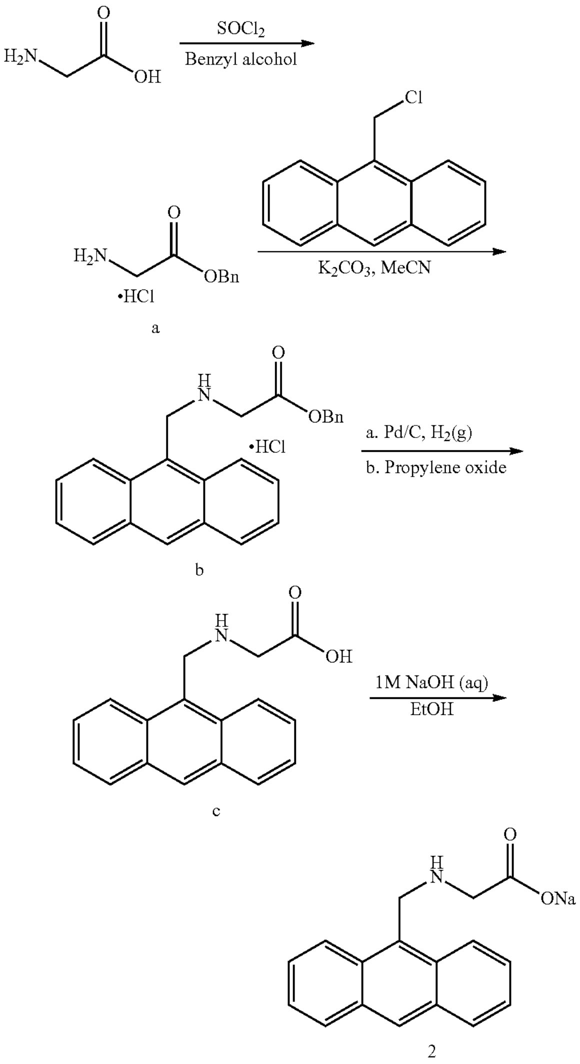

Synthesis Example 1: Synthesis of Compound a in Reaction Scheme 1

3.3 g (20 mmol) of glycine was added to 125 ml of benzyl alcohol, and the resultant was cooled in an ice bath until 0° C. 20 ml of thionyl chloride was drop-wisely added thereto for about 1 hour, placed in an oil bath having a temperature maintained at 110° C., and stirred for about 5 hours to prepare a reaction mixture solution. The reaction mixture solution was cooled to room temperature, and diethylether was added until the solution has turbidity, and the solution was remained in a freezer for 3 hours. Then, a white solid was collected through a filter. The collected white solid was recrystalized using an ethanol-diethylether mixture to obtain 3.0 g (14.8 mmole) of Compound a, glycine benzyl ester hydrochloride, (yield: 74%) as white crystals having a needle shape.

Synthesis Example 2: Synthesis of Compound b in Reaction Scheme 1

3.0 g (15 mmol) of Compound a synthesized in Synthesis Example 1 and 2.1 g (15 mmol) of $K_2CO_3$ were added to 100 ml of acetonitrile in a reactor, and the reactor was filled with nitrogen gas. A solution prepared by dissolving 1.1 g (5 mmol) of 9-(chloromethyl)anthracene in 100 ml of acetonitrile was drop-wisely added thereto to prepare a reaction mixture. The reaction mixture was stirred at room temperature for 7 days, undissolved impurities remaining thereafter were removed from the reaction mixture through a filter, and the reaction mixture was concentrated at a reduced pressure by using a rotary evaporator to prepare a concentrate. Next, a mixture solution including ethyl acetate and hexane (ethyl acetate:hexane=1:2 v/v) was used as an eluent to perform column chromatography on the concentrate. Then, a yellow liquid compound having a viscosity thus obtained was dissolved in 100 ml of diethylether, and the solution was bubbled with dry HCl (g).

Figure 3:
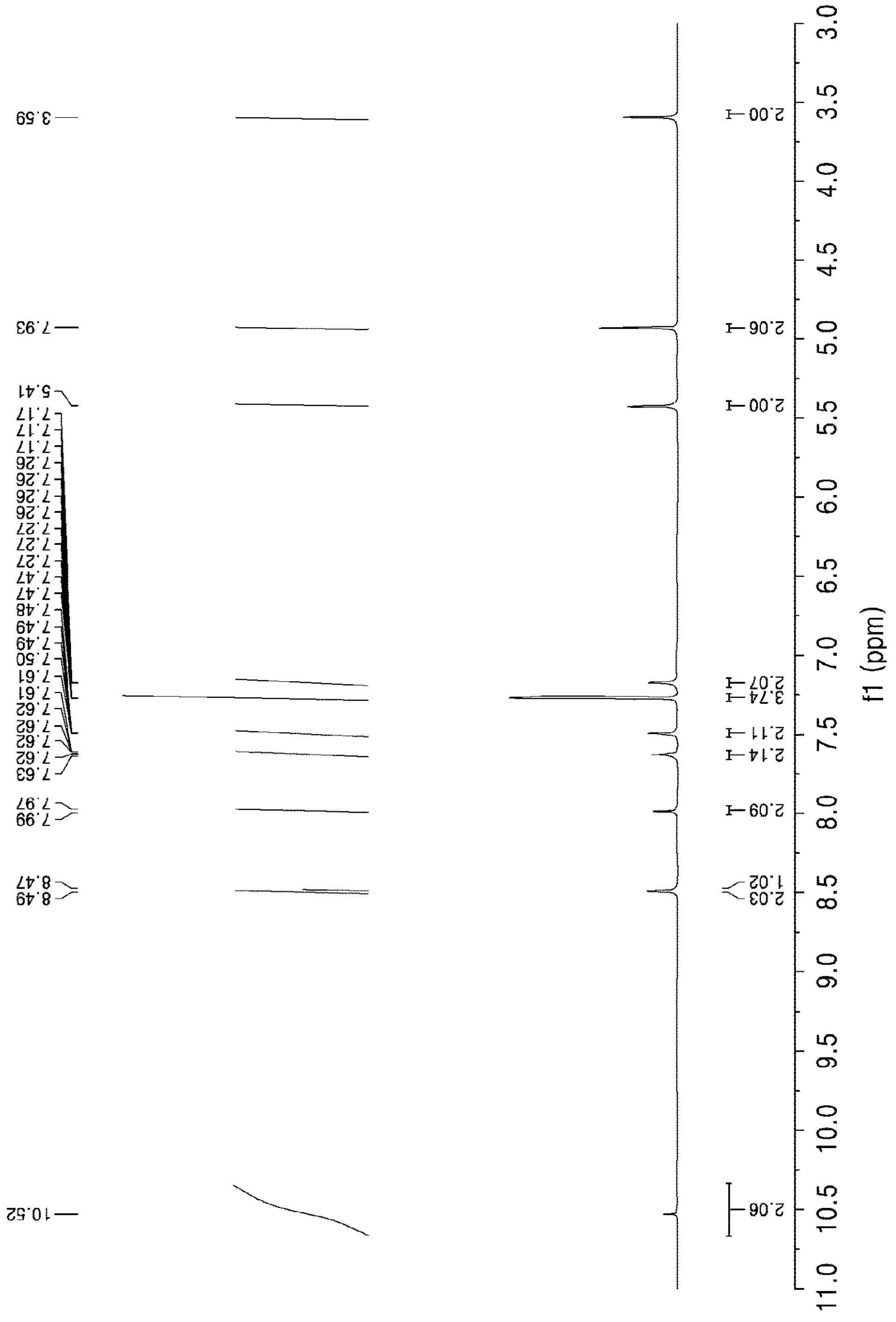
FIG. 3 shows a graph that illustrates the results of $^{1}$H-NMR (600 MHz) spectrum analysis from the spectroscopic analysis results of Compound b prepared in Synthesis Example 2 of Preparation Example L

A white solid obtained after the bubbling process was collected through a filter, and the solid was recrystalized using an ethanol-diethylether mixture to obtain 1.2 g (3.1 mmole) of Compound b, benzyl 2-((anthracen-9-ylmethyl) amino)acetate hydrochloride, (yield: 62%) as white crystals having a needle shape.

mp 191-192° C.; $^1$H-NMR (600 MHz, $CDCl_3$) δ 8.49 (s, 2H), 8.47 (s, 1H), 7.98 (d, 2H, J=8.4 Hz), 7.63 (dd, 1H, J=6.6 Hz, J'=1.2 Hz), 7.61 (dd, 1H, J=6.6 Hz, J'=1.2 Hz), 7.50-7.47 (m, 2H), 7.28-7.25 (m, 31-1), 7.18-7.15 (m, 2H), 5.41 (s, 2H), 4.93 (s, 2H), 3.59 (s, 2H) ppm (FIG. 3)

Figure 4:
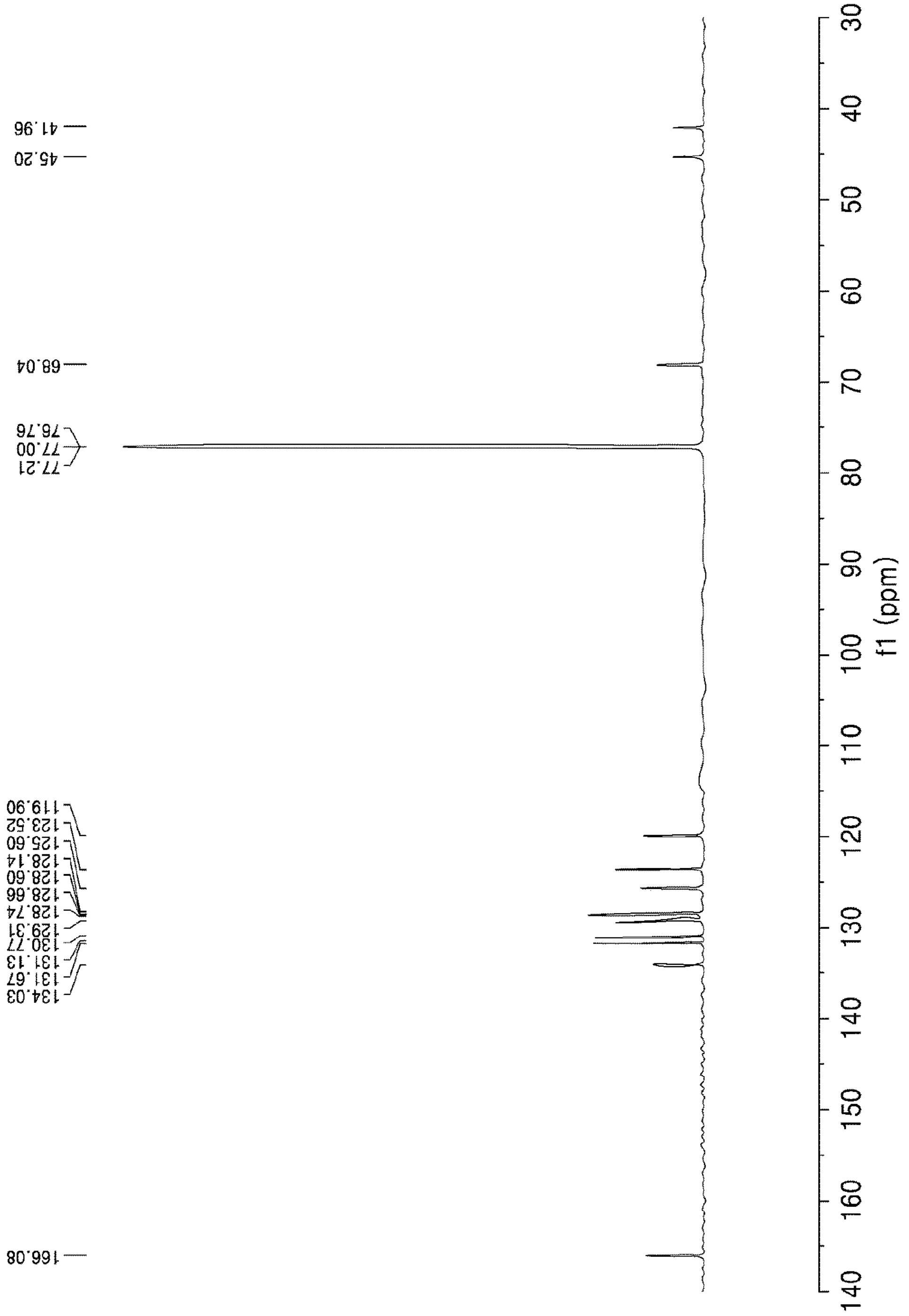
FIG. 4 shows a graph that illustrates the results of $^{13}$C-NMR (150 MHz) spectrum analysis from the spectroscopic analysis results of Compound b prepared in Synthesis Example 2 of Preparation Example 1.

$^{13}$C-NMR (150 MHz, $CDCl_3$) δ 166.08, 134.03, 131.67, 131.13, 130.77, 129.31, 128.74, 128.66, 128.60, 128.14, 125.60, 123.52, 119.90, 68.04, 45.20, 41.96 ppm (FIG. 4)

Figure 5:
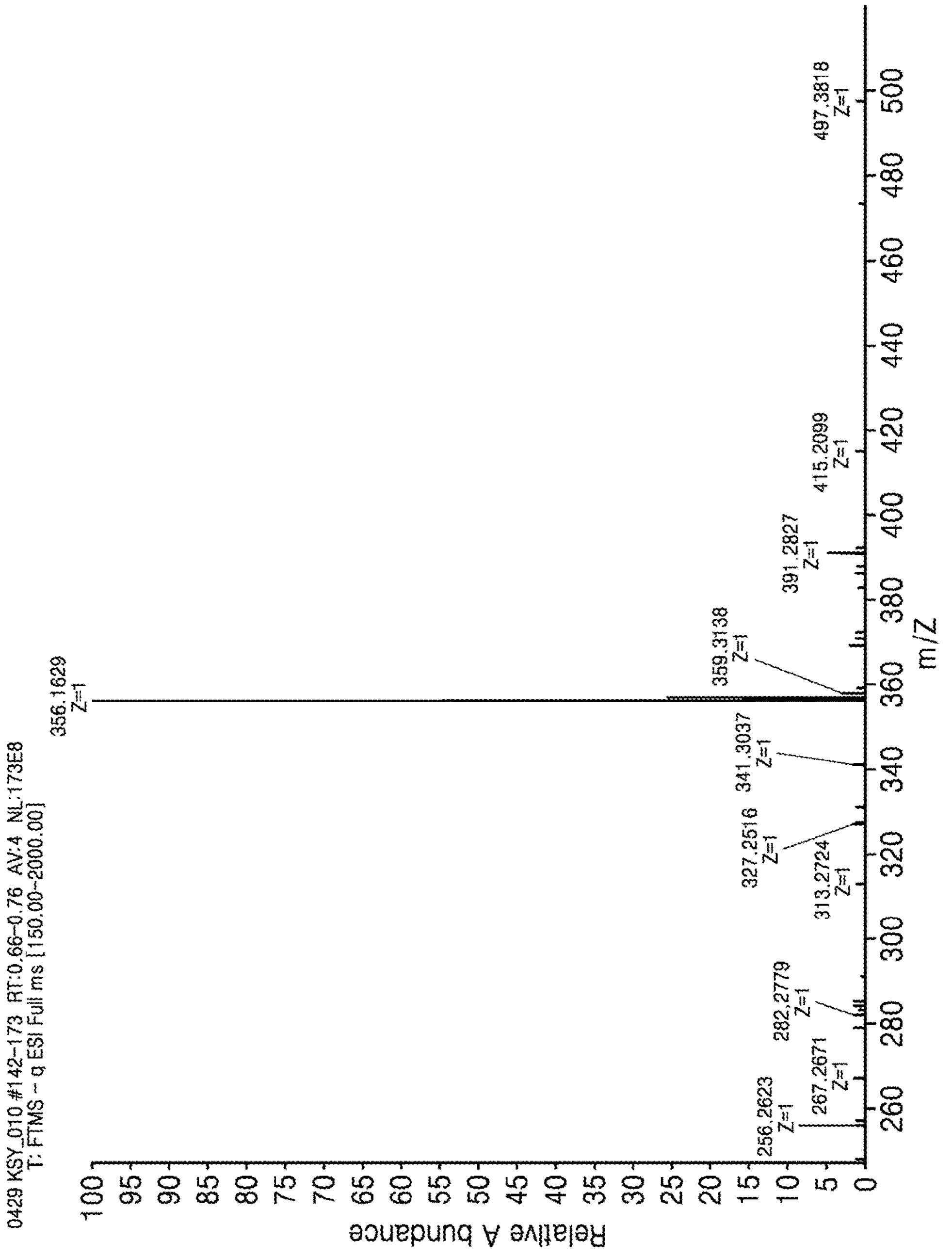
FIG. 5 shows a graph that illustrates the results of HR-MS spectrum analysis from the spectroscopic analysis results of Compound b prepared in Synthesis Example 2 of Preparation Example 1.

HR-MS (ESI) calcd for $C_{24}H_{22}O_2N[M-Cl]^+$356.1645; found 356.1629 (FIG. 5).

Synthesis Example 3: Synthesis of Compound c in Reaction Scheme 1

Figure 6:
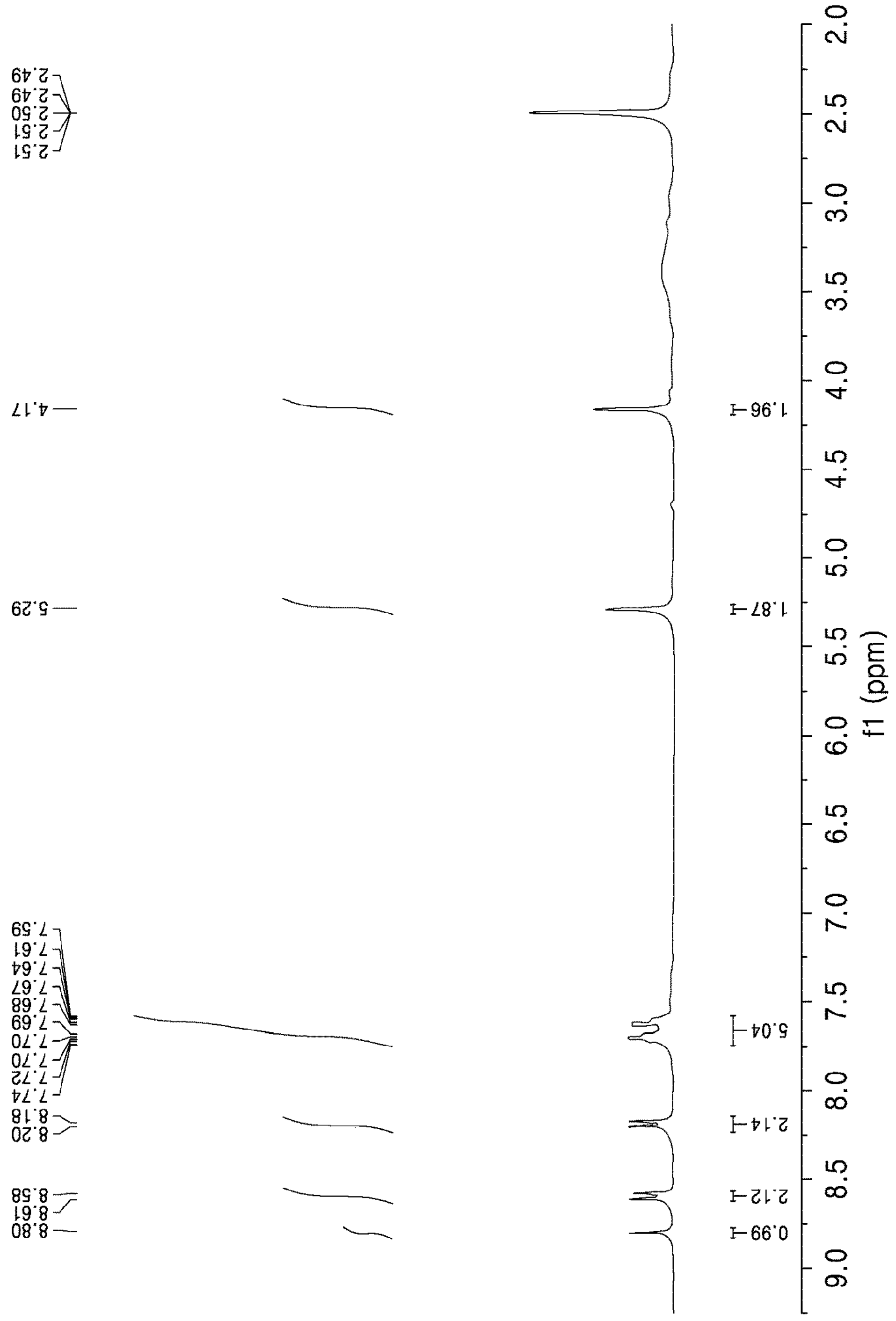
FIG. 6 shows a graph that illustrates the results of $^{1}$H-NMR (300 MHz) spectrum analysis from the spectroscopic analysis results of Compound c prepared in Synthesis Example 3 of Preparation Example 1.

0.78 g (2 mmole) of Compound b prepared in Synthesis Example 2 was dissolved in 40 ml of ethanol, stirred while maintaining hydrogen gas at room pressure at room temperature for 4 hours by using 10% palladium-carbon as a catalyst to prepare a suspension. Then, the suspension was filtered through a celite pad, and the resultant was collected and concentrated at a reduced pressure by using a rotary evaporator to prepare a reaction mixture. The reaction mixture was dissolved in 30 ml of ethanol, cooled in an ice bath until the temperature was 0° C., and then 7 ml of propylene oxide was drop-wisely added thereto. The resultant was refluxed for 1 hour, and slowly cooled to room temperature, and the precipitate thus produced was collected by using a filter, and recrystalized using a water-ethanol mixture to obtain 0.347 g (1.31 mmole) of Compound c, 2-((anthracen-9-ylmethyl)amino)aceticacid), (yield: 66%). Here, Compound c was not soluble in a solvent such as $CDCl_3$, DMSO-$d_6$, $CD_3OD$, or $D_2O$, and thus the NMR spectrum of Compound c was obtained by using a HCl salt form of Compound c.

mp 229-230° C.; $^1$H-NMR (300 MHz, DMSO-$d_6$) δ 8.80 (s, 1H), 8.60 (d, 2H, J=9.7 Hz), 8.19 (d, 2H, J=8.7 Hz), 7.74-7.59 (m, 4H), 5.29 (s, 2H), 4.17 (s, 2H) ppm (FIG. 6)

Figure 7:
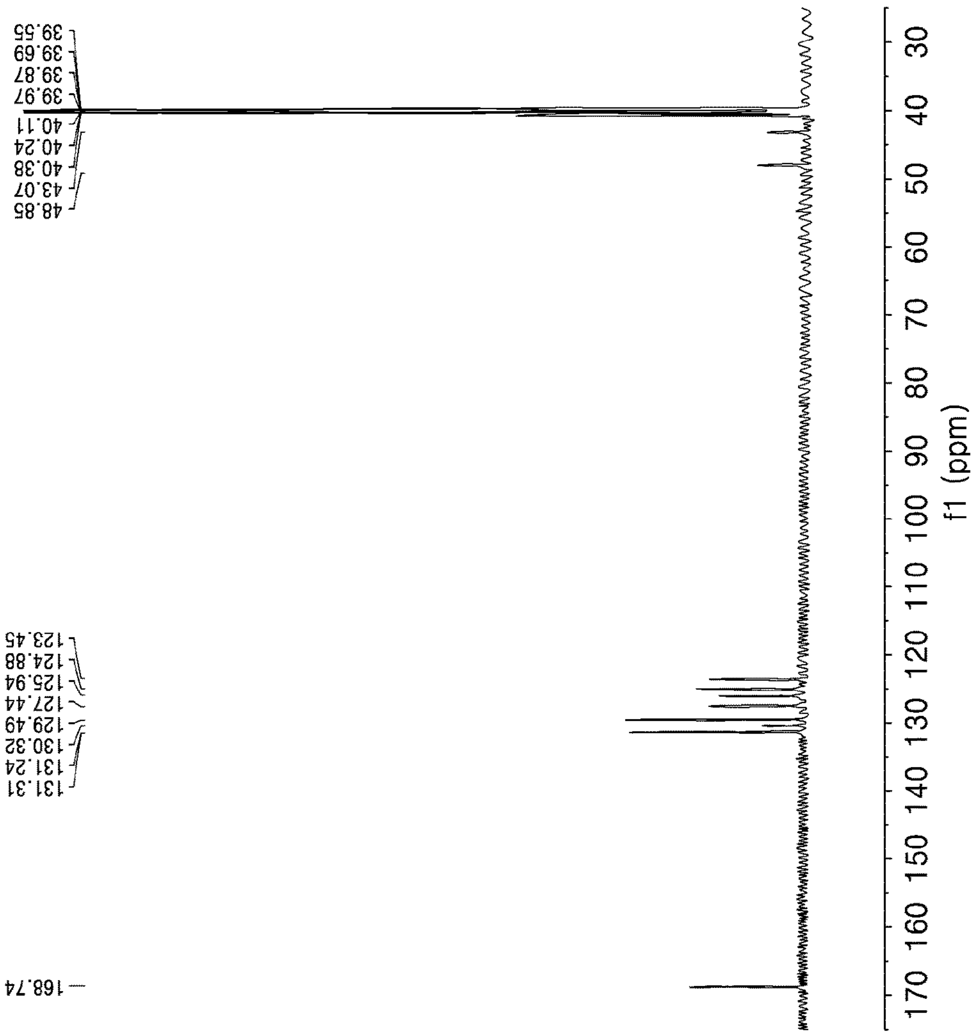
FIG. 7 shows a graph that illustrates the results of $^{13}$C-NMR (150 MHz) spectrum analysis from the spectroscopic analysis results of Compound c prepared in Synthesis Example 3 of Preparation Example 1.

$^{13}$C-NMR (150 MHz, DMSO-$d_6$) δ 168.71, 131.31, 131.24, 130.32, 129.49, 127.44, 125.94, 124.88, 123.45, 47.85, 43.07 ppm (FIG. 7)

Figure 8:
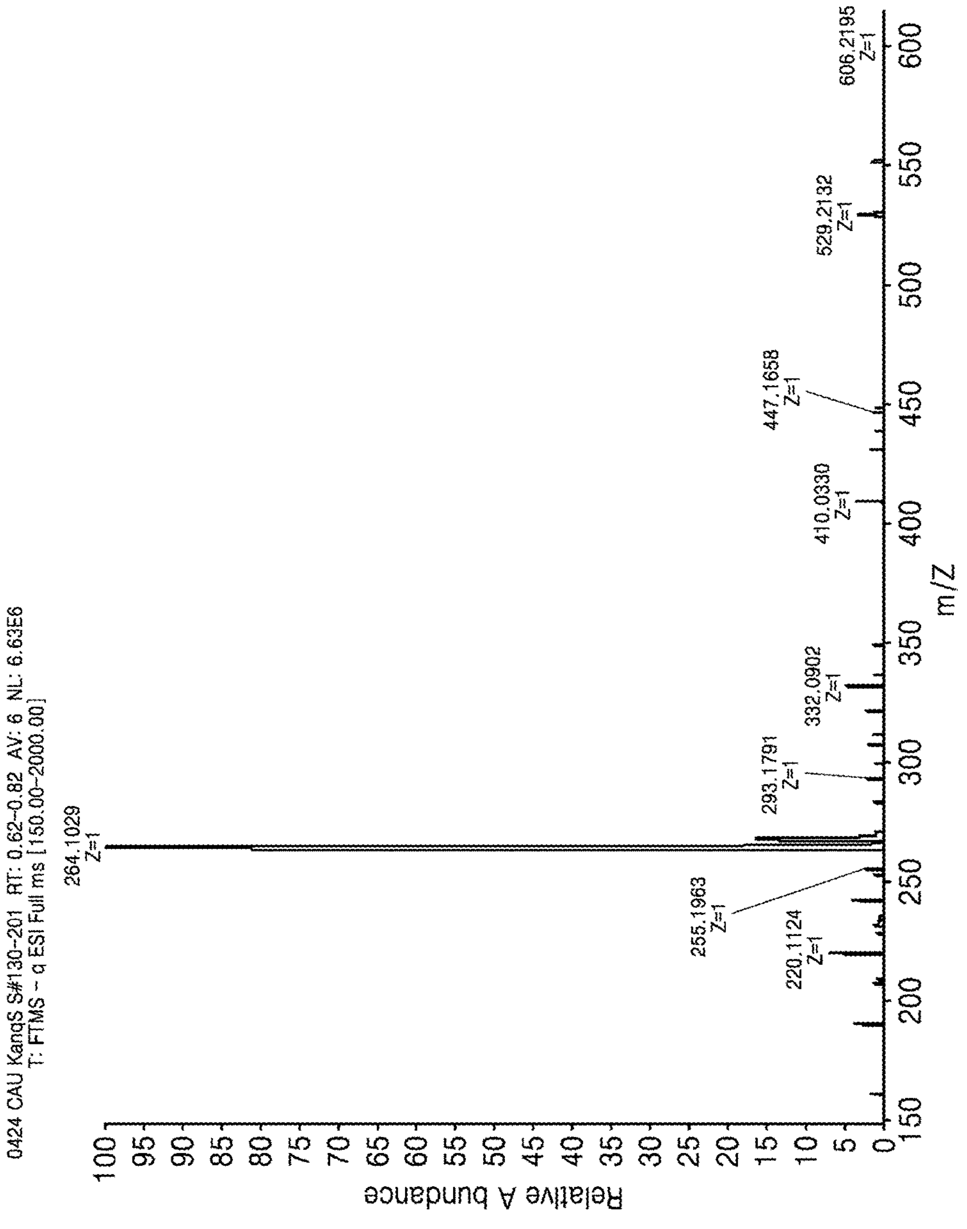
FIG. 8 shows a graph that illustrates the results of HR-MS spectrum analysis from the spectroscopic analysis results of Compound c prepared in Synthesis Example 3 of Preparation Example 1.

HR-MS (ESI) calcd for $C_{17}H_{14}O_2N[M-H]^-$ 264.1019; found 264.1029 (FIG. 8).

Synthesis Example 4: Synthesis of Compound Represented by Formula 2 in Reaction Scheme 1

0.072 g (0.27 mmole) of Compound c synthesized in Synthesis Example 3 was added to 50 ml of ethanol, and the resultant was cooled in an ice bath until its temperature was 0° C. 0.27 ml of 1 M NaOH(aq) was slowly and drop-wisely added thereto, and the mixture was stirred for 30 minutes while maintaining the temperature at 0° C. to prepare a reaction mixture. The reaction mixture was concentrated at a reduced pressure by using a rotary evaporator to obtain 0.070 g (0.244 mmole) of a compound represented by Formula 2, sodium 2-((anthracen-9-ylmethyl)amino)acetat, (yield: 90%) as a light yellow solid compound.

Figure 9:
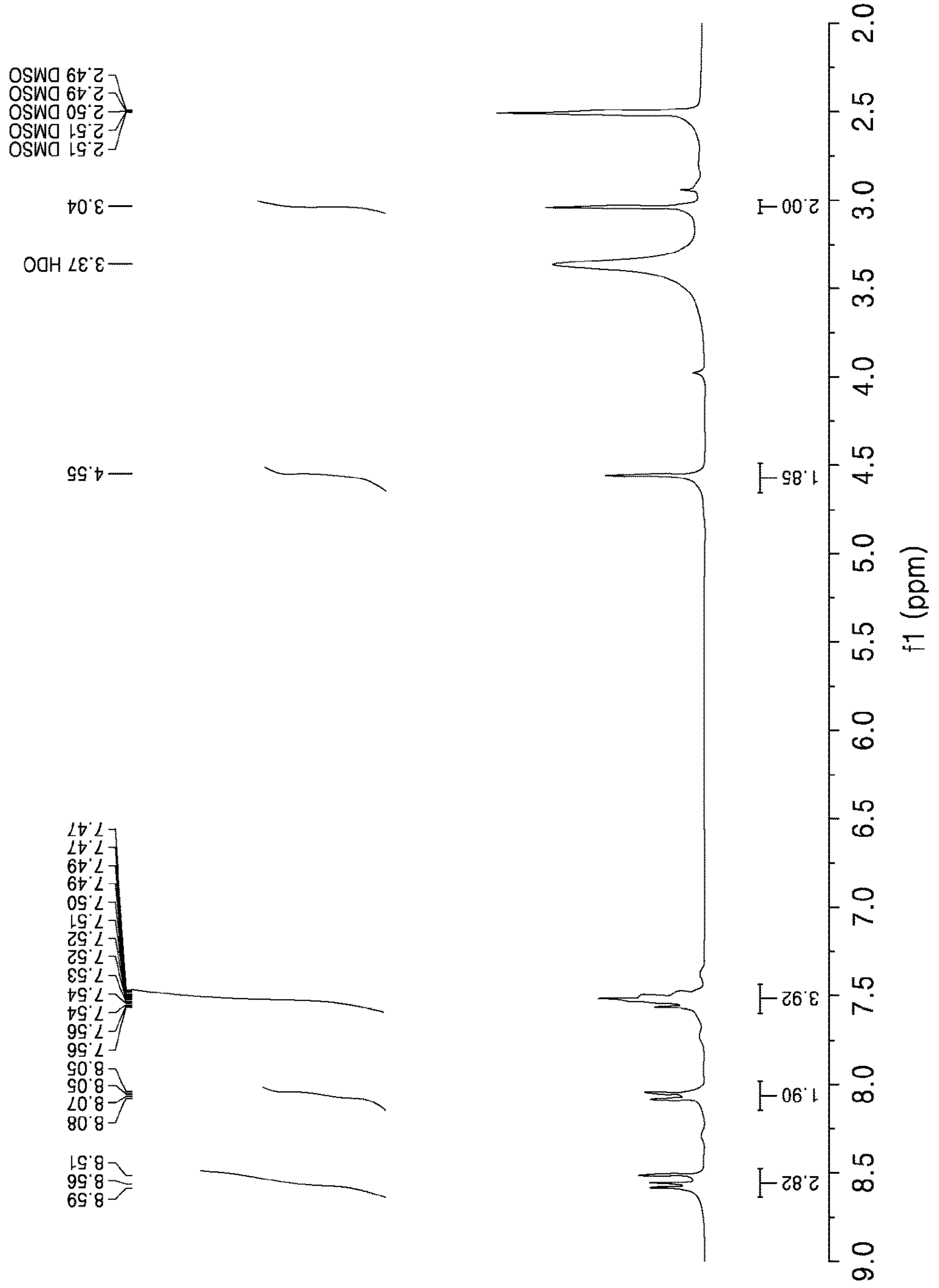
FIG. 9 shows a graph that illustrates the results of $^{1}$H-NMR (300 MHz) spectrum analysis from the spectroscopic analysis results of a compound represented by Formula 2 prepared in Synthesis Example 4 of Preparation Example 1.

$^1$H-NMR (300 MHz, DMSO-$d_6$) δ 8.59 (d, 2H, J=9.7 Hz), 8.51 (s, 1H), 8.06 (d, 2H, J=8.3 Hz), 7.56-7.47 (m, 4H), 4.55 (s, 2H), 3.04 (s, 2H) ppm (FIG. 9)

Figure 10:
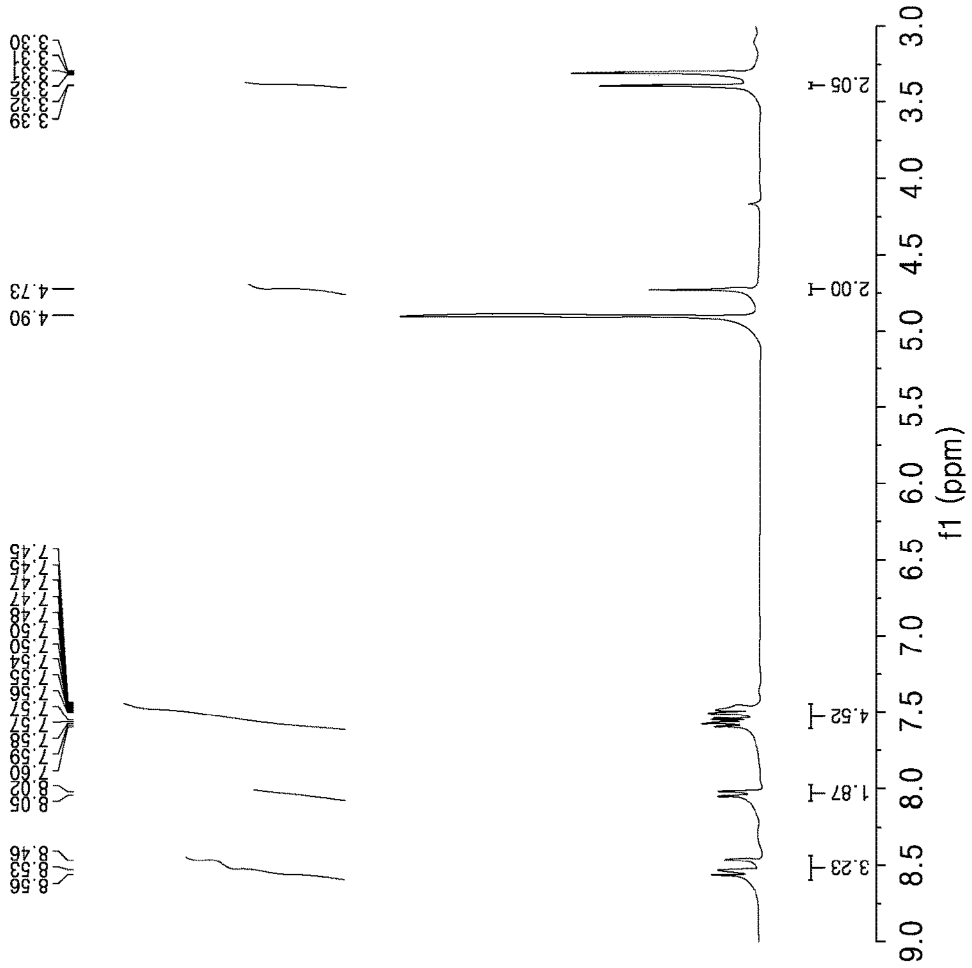
FIG. 10 shows a graph that illustrates the results of $^{1}$H-NMR (300 MHz) spectrum analysis from the spectroscopic analysis results of the compound represented by Formula 2 prepared in Synthesis Example 4 of Preparation Example 1.
Figure 11:
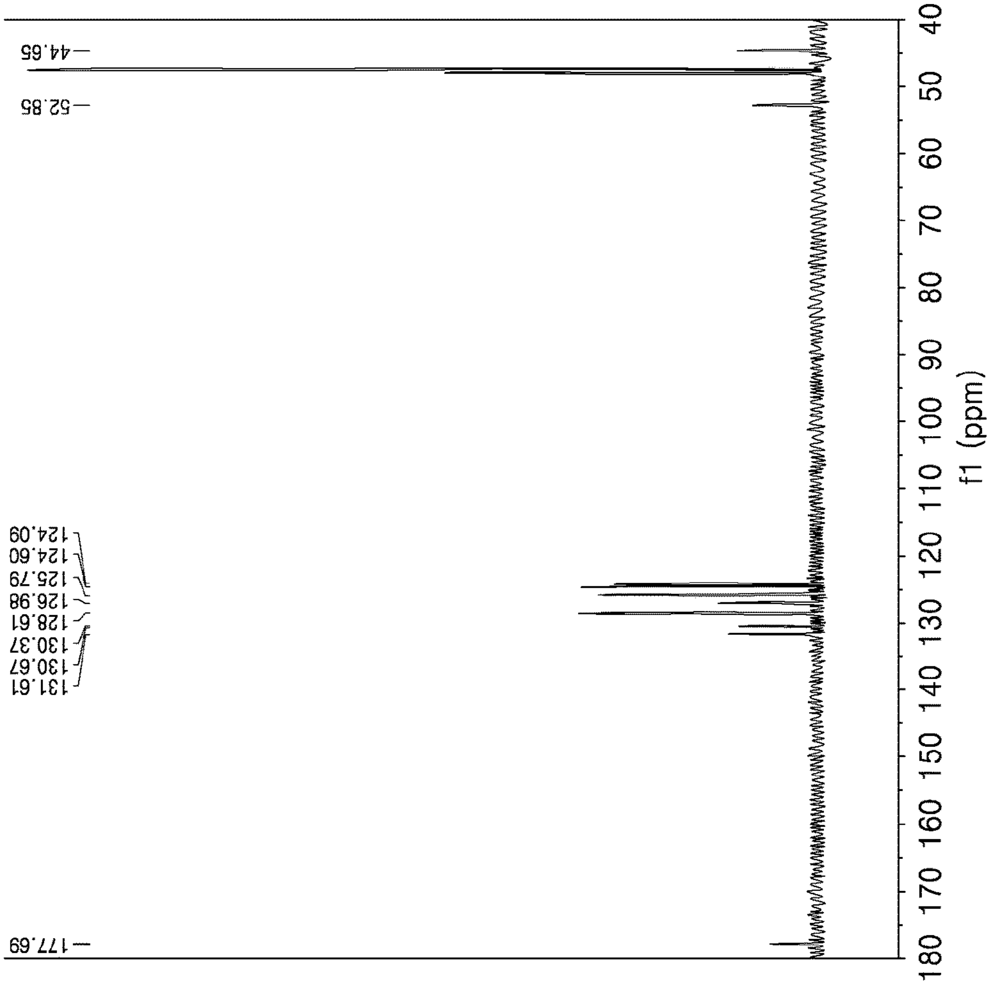
FIG. 11 shows a graph that illustrates the results of $^{13}$C-NMR (150 MHz) spectrum analysis from the spectroscopic analysis results of the compound represented by Formula 2 prepared in Synthesis Example 4 of Preparation Example 1.

$^1$H-NMR (300 MHz, $CD_3OD$) δ 8.55 (d, 2H, J=10.0 Hz), 8.46 (s, 1H), 8.04 (d, 2H, J=9.3 Hz), 7.60-7.45 (m, 4H), 4.73 (s, 2H), 3.39 (s, 2H) ppm (FIG. 10) $^{13}$C-NMR (150 MHz, $CD_3OD$) δ 177.69, 131.61, 130.67, 130.37, 128.61, 126.98, 125.79, 124.60, 124.09, 52.85, 44.65 ppm (FIG. 11)

Figure 12:
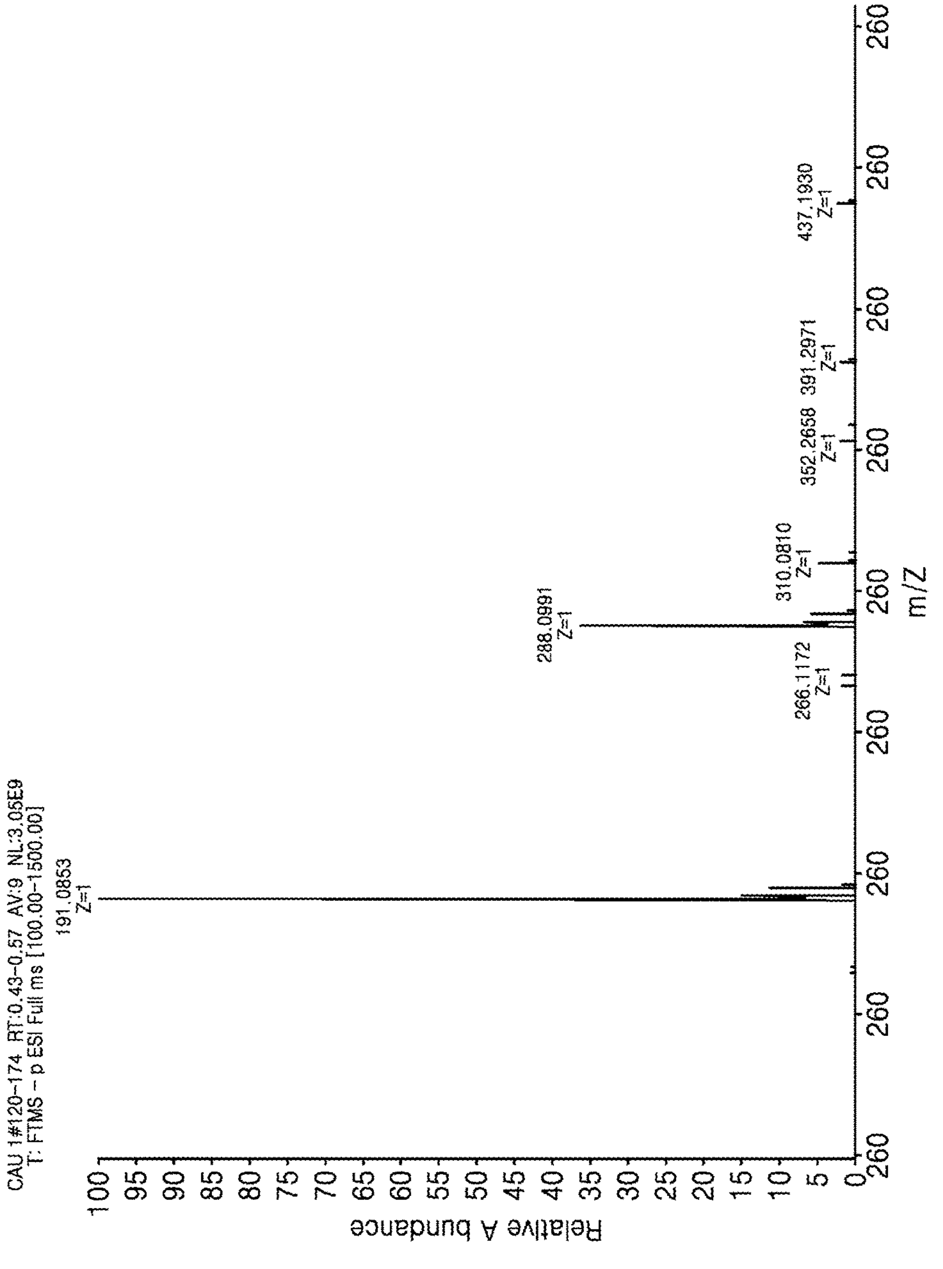
FIG. 12 shows a graph that illustrates the results of FIR-MS spectrum analysis from the spectroscopic analysis results of the compound represented by Formula 2 prepared in Synthesis Example 4 of Preparation Example 1.

HRMS (ESI) calcd for $C_{17}H_{15}NO_2Na[M+H]^+$ 288.0995; found 288.0991 (FIG. 12).

Preparation Example 2. Preparation of Compound Represented by Formula 3 in Reaction Scheme 2

[Reaction scheme 2]

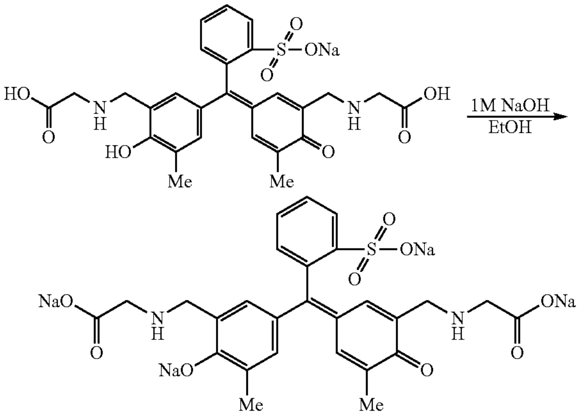

Formula 3

0.110 g (0.190 mmole) of glycine cresol red sodium salt was dissolved in 40 ml of EtOH, and the solution was cooled in an ice bath until its temperature was 0° C. Then, 0.57 ml (0.57 mmole) of 1 M NaOH(aq) was slowly and drop-wisely added thereto, stirred at 0° C. for about 2 hours, and concentrated at a reduced pressure by using a rotary evaporator. The resultant was finally dried using a schlenk line to obtain a compound represented by Formula 3 as a purple solid compound at a quantitative yield.

Preparation Example 3. Preparation of Compound Represented by Formula 5

Figure 16:
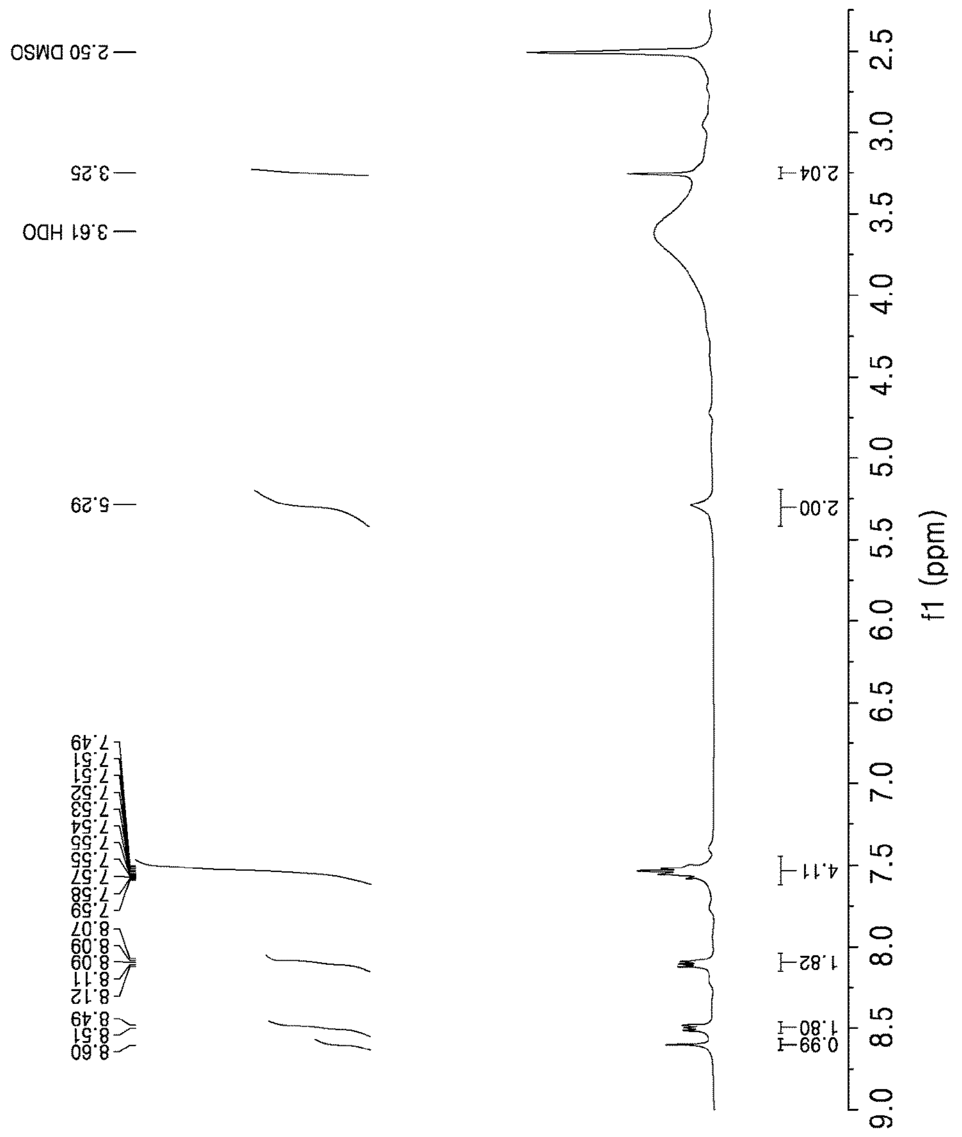
FIG. 16 shows a graph that illustrates the results of $^{1}$H-NMR (300 MHz, DMSO-$d_6$) spectrum analysis from the spectroscopic analysis results of a compound represented by Formula 5 prepared in Preparation Example 3.
Figure 17:
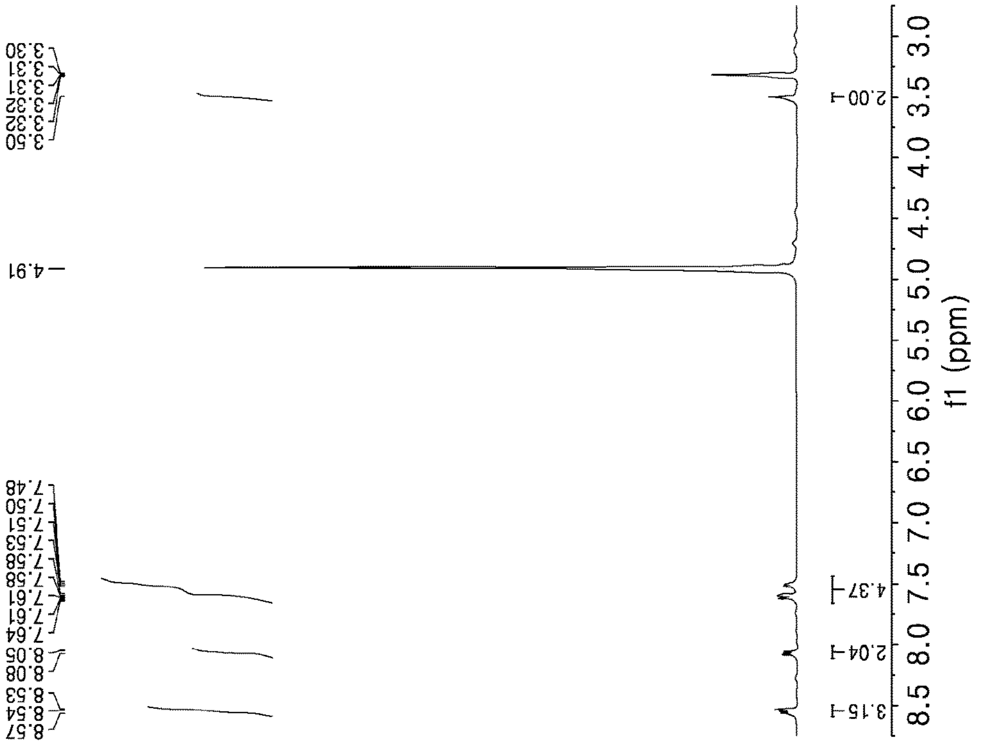
FIG. 17 shows a graph that illustrates the results of $^{1}$H-NMR (300 MHz, $CD_3OD$) spectrum analysis from the spectroscopic analysis results of the compound represented by Formula 5 prepared in Preparation Example 3.

0.3 ml of a solution including the compound represented by Formula 2 synthesized in Preparation Example 1 at a concentration of 0.5 M was mixed with 2.7 ml of anhydrous ethanol, and the mixture was bubbled with a gas mixture including carbon dioxide ($CO_2$) and nitrogen ($N_2$) ($CO_2$: $N_2$=1:9) at a flow rate of 0.6 ml/min, 0.06 ml of carbon dioxide per each bubbling, to obtain a compound represented by Formula 5. Here, the results analyzed by using $^1$H-NMR (300 MHz, DMSO-$d_6$) and $^1$H-NMR (300 MHz, $CD_3OD$) spectrums among the spectroscopic analysis results are shown in FIG. 16 and FIG. 17, respectively.

[Formula 5]

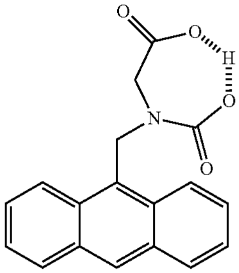

Preparation Example 4. Preparation of Compound Represented by Formula 6

0.3 ml of a solution including the compound represented by Formula 3 synthesized in Preparation Example 2 at a concentration of 0.5 M was mixed with 2.7 ml of anhydrous ethanol, and the mixture was bubbled with a gas mixture including carbon dioxide ($CO_2$) and nitrogen ($N_2$) ($CO_2$: $N_2$=1:9) at a flow rate of 0.6 ml/min, 0.06 ml of carbon dioxide per each bubbling, to obtain a compound represented by Formula 6.

[Formula 6]

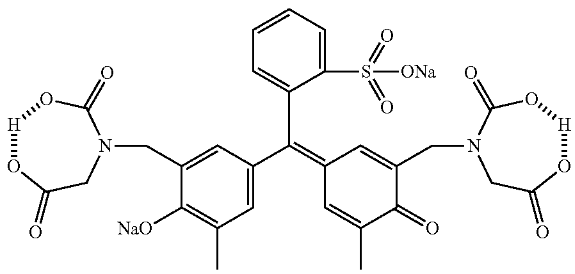

Comparative Example 1. Preparation of Compound Represented by Formula

A compound represented by Formula 7, 9-(Methylaminomethyl)anthracene, having a purity of 99% available from Sigma-Aldrich was purchased and used without further purification.

[Formula 7]

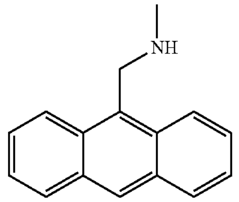

Comparative Example 2. Preparation of Compound Represented by Formula 8 in Reaction Scheme 3

[Reaction scheme 3]

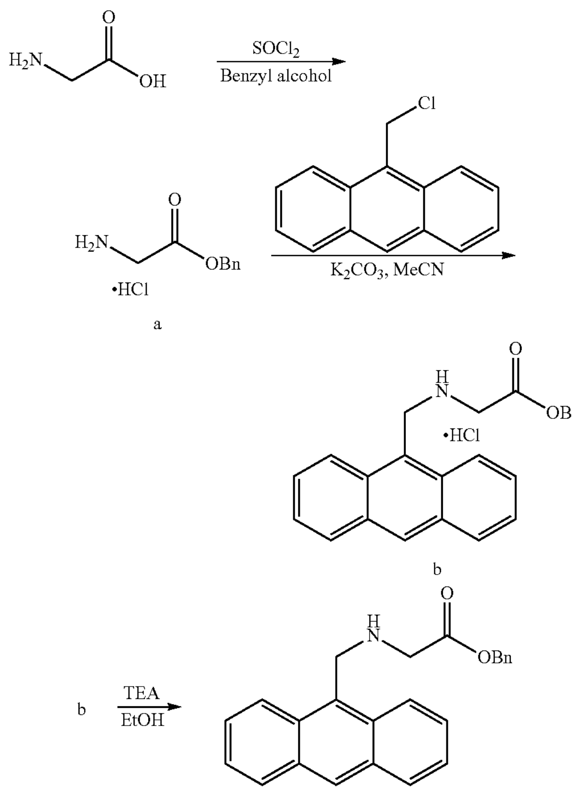

a b

Formula 8

Synthesis Example 1: Synthesis of Compound a in Reaction Scheme 3

3.3 g (20 mmol) of glycine was added to 125 ml of benzyl alcohol, and the resultant was cooled in an ice bath until 0° C. 20 ml of thionyl chloride was drop-wisely added thereto for about 1 hour, placed in an oil bath having a temperature maintained at 110° C., and stirred for about 5 hours to prepare a reaction mixture solution. The reaction mixture solution was cooled to room temperature, and diethylether was added until the solution has turbidity, and the solution was remained in a freezer for 3 hours. Then, a white solid was collected through a filter. The collected white solid was recrystalized using an ethanol-diethylether mixture to obtain 3.0 g (14.8 mmole) of compound a, glycine benzyl ester hydrochloride, (yield: 74%) as white crystals having a needle shape.

Synthesis Example 2: Synthesis of Compound b in Reaction Scheme 3

3.0 g (15 mmol) of Compound a synthesized in Synthesis Example 1 and 2.1 g (15 mmol) of $K_2CO_3$ were added to 100 ml of acetonitrile in a reactor, and the reactor was filled with nitrogen gas. A solution prepared by dissolving 1.1 g (5 mmol) of 9-(chloromethyl)anthracene in 100 ml of acetonitrile was drop-wisely added thereto to prepare a reaction mixture. The reaction mixture was stirred at room temperature for 7 days, undissolved impurities remaining thereafter were removed from the reaction mixture through a filter, and the reaction mixture was concentrated at a reduced pressure by using a rotary evaporator to prepare a concentrate. Next, a mixture solution including ethyl acetate and hexane (ethyl acetate:hexane=1:2 v/v) was used as an eluent to perform column chromatography on the concentrate. Then, a yellow liquid compound having a viscosity thus obtained was dissolved in 100 ml of diethylether, and the solution was bubbled with dry HCl(g).

A white solid obtained after the bubbling process was collected through a filter, and the solid was recrystalized using an ethanol-diethylether mixture to obtain 1.2 g (3.1 mmole) of Compound b, benzyl 2-((anthracen-9-ylmethyl)amino)acetate hydrochloride, (yield: 62%) as white crystals having a needle shape.

mp 191-192° C.; $^1$H-NMR (600 MHz, $CDCl_3$) δ 8.49 (s, 2H), 8.47 (s, 1H), 7.98 (d, 2H, J=8.4 Hz), 7.63 (dd, 1H, J=6.6 Hz, J'=1.2 Hz), 7.61 (dd, 1H, J=6.6 Hz, J'=1.2 Hz), 7.50-7.47 (m, 2H), 7.28-7.25 (m, 3H), 7.18-7.15 (m, 2H), 5.41 (s, 2H), 4.93 (s, 2H), 3.59 (s, 2H) ppm (FIG. 3)

$^{13}$C-NMR (150 MHz, $CDCl_3$) δ 166.08, 134.03, 131.67, 131.13, 130.77, 129.31, 128.74, 128.66, 128.60, 128.14, 125.60, 123.52, 119.90, 68.04, 45.20, 41.96 ppm (FIG. 4)

HRMS (ESI) calcd for $C_{24}H_{22}O_2N[M-Cl]^+$ 356.1645; found 356.1629 (FIG. 5).

Synthesis Example 3. Synthesis of Compound Represented by Formula 8

0.102 g (0.26 mmole) of Compound b prepared in Synthesis Example 2 was dissolved in 10 ml of ethanol, the solution was cooled in an ice bath until its temperature was 0° C., and then 0.04 ml (0.29 mmole) of triethylamine was drop-wisely added to the solution. Then, while the temperature was maintained at 0° C., the solution was stirred for 1 hour and concentrated at a reduced pressure by using a rotary evaporator to prepare a reaction mixture. The reaction mixture was dissolved in 10 ml of dichloromethane and washed three times with brine, 10 ml each time.

Thereafter, the dichloromethane layer was collected to remove water remained in the dichloromethane layer by using anhydrous $Na_2SO_4$(s), and the filtrate after filtering the resultant was concentrated at a reduced pressure to obtain 0.071 g (0.20 mmole) of a compound represented by Formula 3, benzyl 2-((anthracen-9-ylmethyl)amino)acetate, (yield: 77%) as a yellow liquid having a viscosity.

Figure 13:
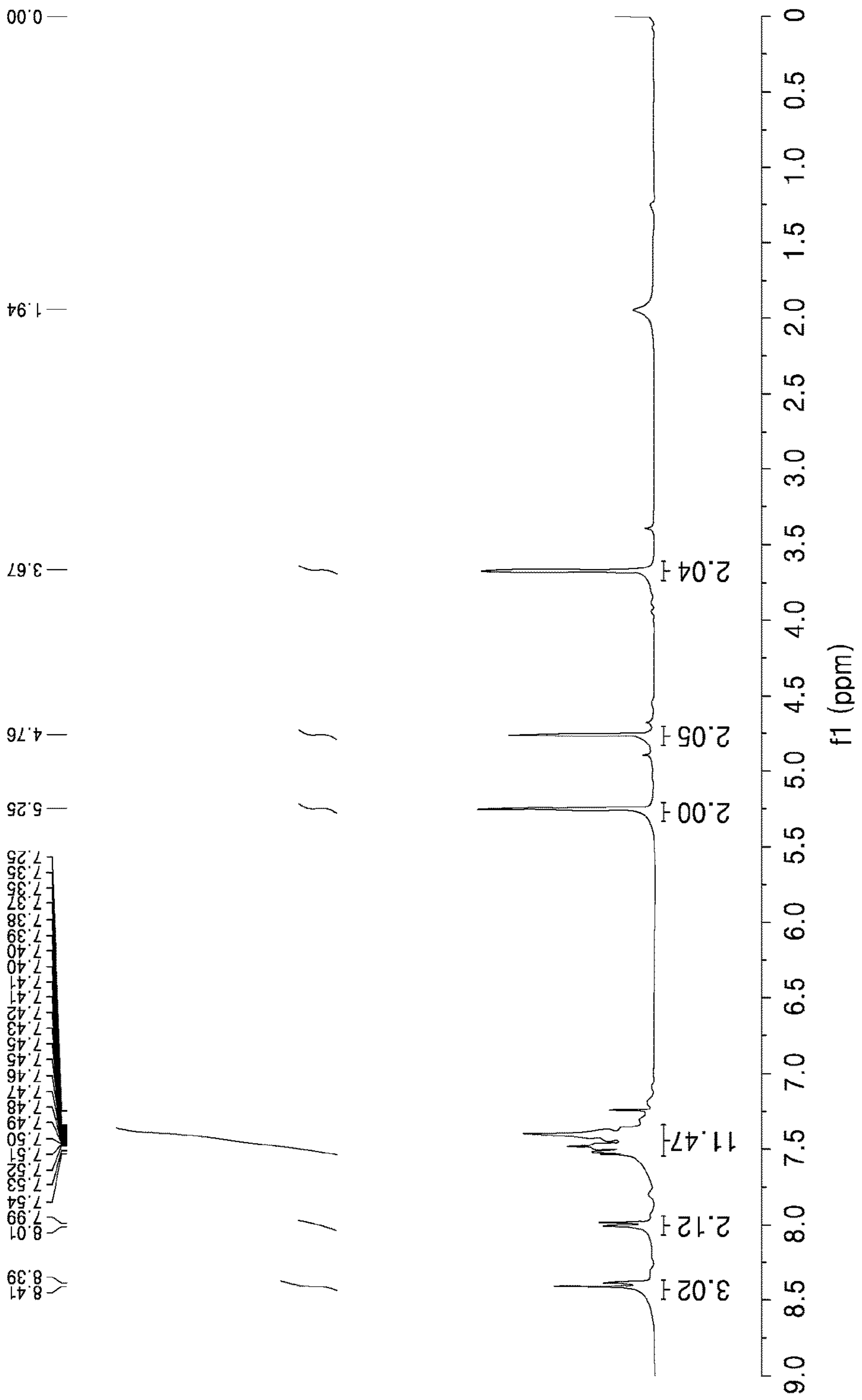
FIG. 13 shows a graph that illustrates the results of $^{1}$H-NMR (300 MHz) spectrum analysis from the spectroscopic analysis results of a compound represented by Formula 8 prepared in Synthesis Example 3 of Comparative Example 2.

$^1$H-NMR (300 MHz, $CDCl_3$) δ 8.41 (s, 2H), 8.39 (s, 1H), 8.00 (d, 2H, J=9.0 Hz), 7.54-7.25 (m, 9H), 5.25 (s, 2H), 4.76 (s, 2H), 3.67 (s, 2H) ppm (FIG. 13)

Figure 14:
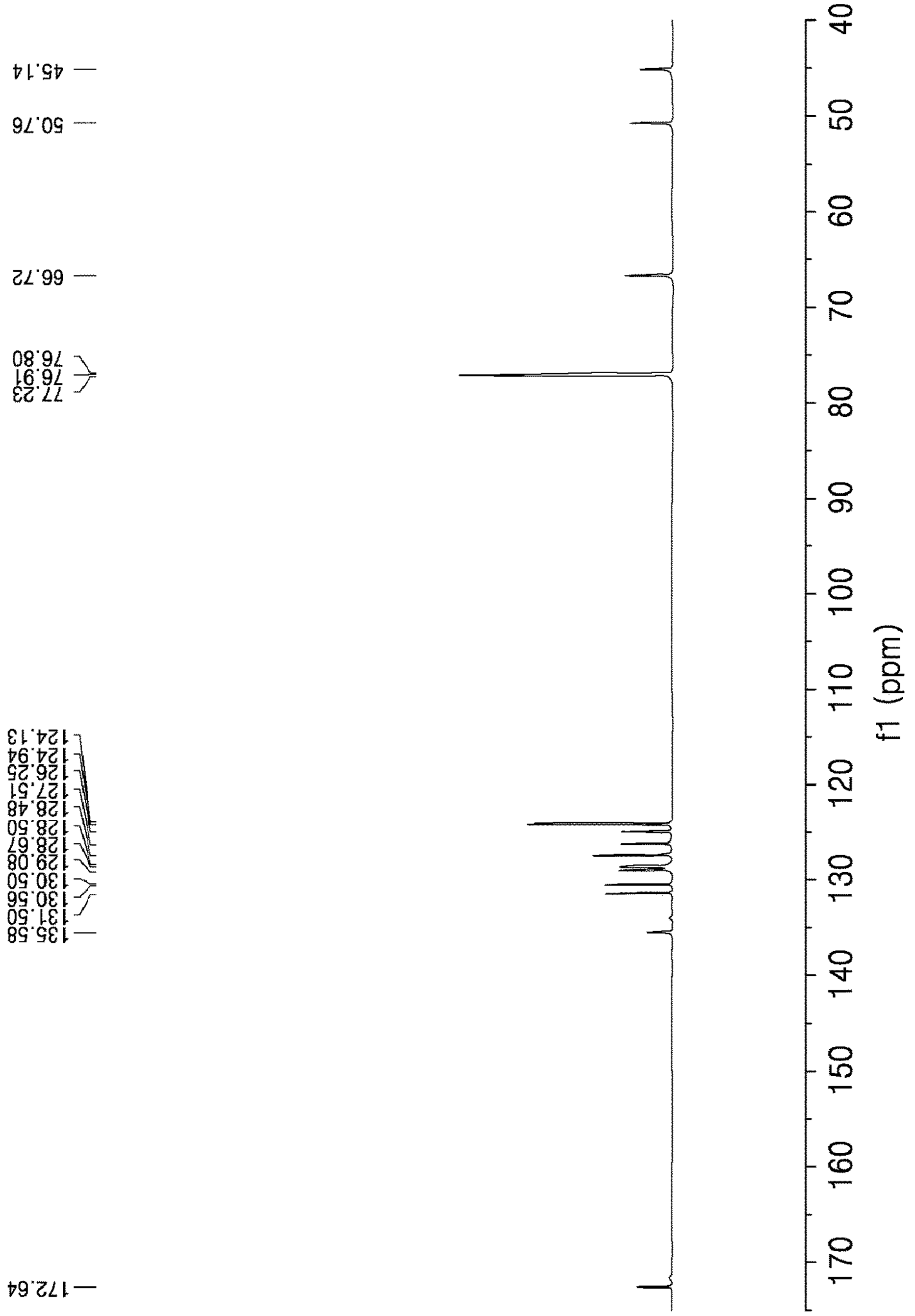
FIG. 14 shows a graph that illustrates the results of $^{13}$C-NMR (150 MHz) spectrum analysis from the spectroscopic analysis results of the compound represented by Formula 8 prepared in Synthesis Example 3 of Comparative Example 2.

$^{13}$C-NMR (150 MHz, $CDCl_3$) δ 172.64, 135.58, 131.50, 130.56, 130.50, 129.08, 128.67, 128.50, 128.48, 127.51, 126.25, 124.94, 124.13, 66.72, 50.76, 45.14 ppm (FIG. 14)

Figure 15:
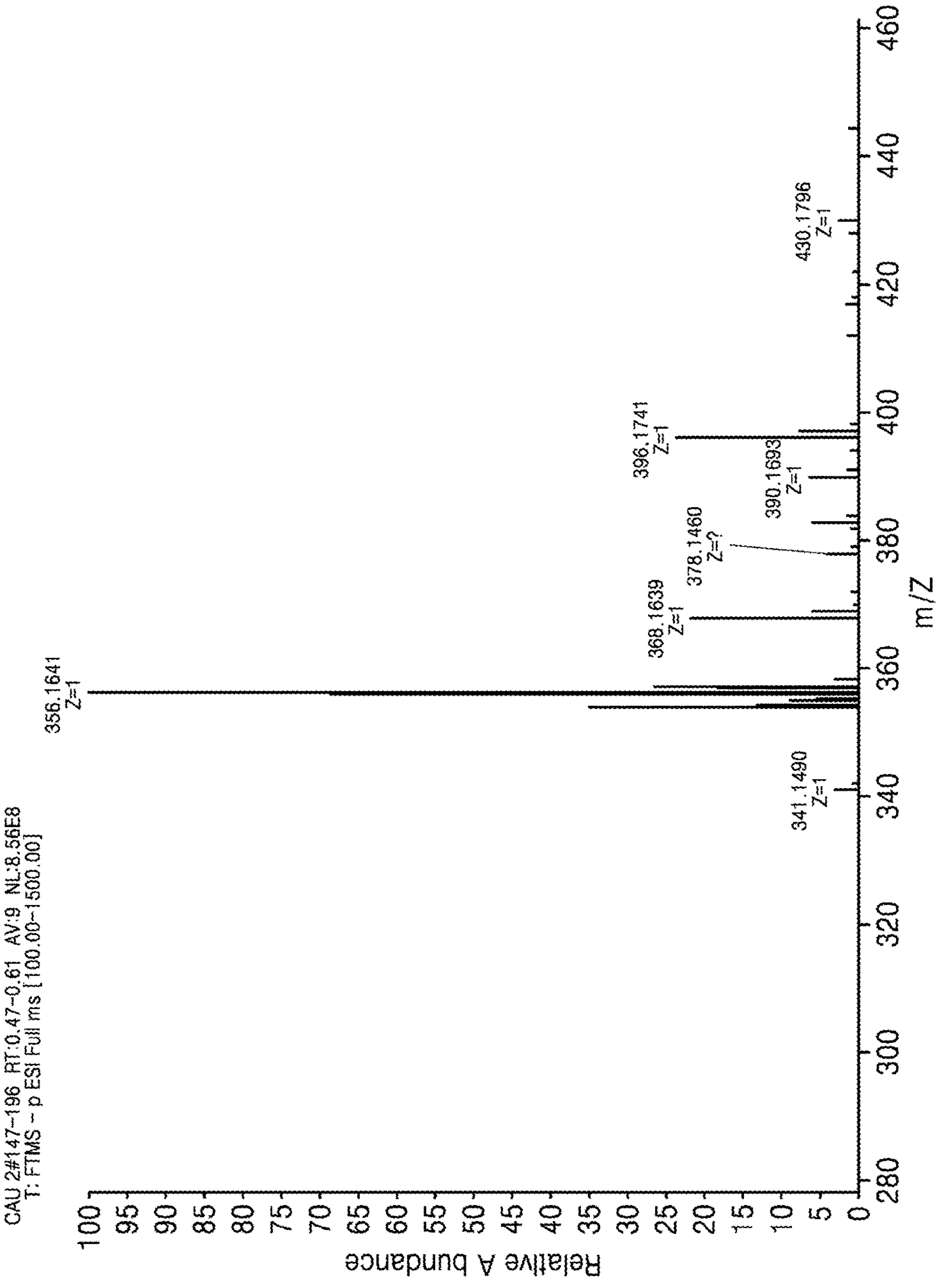
FIG. 15 shows a graph that illustrates the results of HR-MS spectrum analysis from the spectroscopic analysis results of the compound represented by Formula 8 prepared in Synthesis Example 3 of Comparative Example 2.

HR-MS (ESI) calcd for $C_{24}H_{22}O_2N[M+H]^+$ 356.1645; found 356.1641 (FIG. 15).

Comparative Example 3: Compound Represented by Formula 9

0.3 ml of a solution including the compound represented by Formula 7 synthesized in Comparative Example 1 at a concentration of 0.5 M was mixed with 2.7 ml of anhydrous ethanol, and the mixture was bubbled with a gas mixture including carbon dioxide ($CO_2$) and nitrogen ($N_2$) ($CO_2$:

$N_2$=1:9) at a flow rate of 0.6 ml/min, 0.06 ml of carbon dioxide per each bubbling, to obtain a compound represented by Formula 9.

[Formula 9]

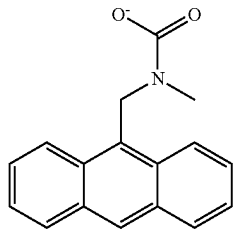

Comparative Example 4. Compound Represented by Formula 10

0.3 ml of a solution including the compound represented by Formula 8 synthesized in Comparative Example 2 at a concentration of 0.5 M was mixed with 2.7 ml of anhydrous ethanol, and the mixture was bubbled with a gas mixture including carbon dioxide ($CO_2$) and nitrogen ($N_2$) ($CO_2$: $N_2$=1:9) at a flow rate of 0.6 ml/min, 0.06 ml of carbon dioxide per each bubbling, to obtain a compound represented by Formula 10.

[Formula 10]

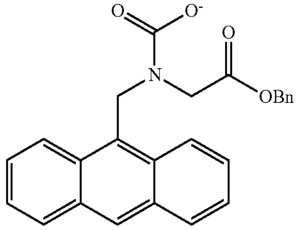

Experimental Example 1

1) The compound (Formula 2) prepared in Preparation Example 1, the compound (Formula 7) prepared in Comparative Example 1, and the compound (Formula 8) prepared in Comparative Example 2 were each dissolved in anhydrous ethanol to have a concentration of 0.5 M, and thus a stock solution for each of the compounds was prepared.

Here, the anhydrous ethanol was provided with an excessive amount of nitrogen so that all other dissolved gas was completely removed before the use.

2) 0.3 ml of each of the stock solutions (prepared by dissolving each of the compounds of Preparation Example 1, Comparative Example 1, and Comparative Example 2) was mixed with 2.7 ml of anhydrous ethanol, and the mixture was bubbled with a gas mixture including carbon dioxide ($CO_2$) and nitrogen ($N_2$) ($CO_2$: $N_2$=1:9) at a flow rate of 0.6 ml/min, 0.06 ml of carbon dioxide per each bubbling, and a fluorescent spectrum thereof was obtained, and the result is shown in FIG. 16. In order to confirm reproducibility of the experiment, the experiment was repeated 3 times, and an average value of the measured values was recorded.

Here, an excitation wavelength during the fluorescence measurement was determined to be 365 nm through the experiment, and an emission wavelength was confirmed from 380 nm to 600 nm.

Figure 18:
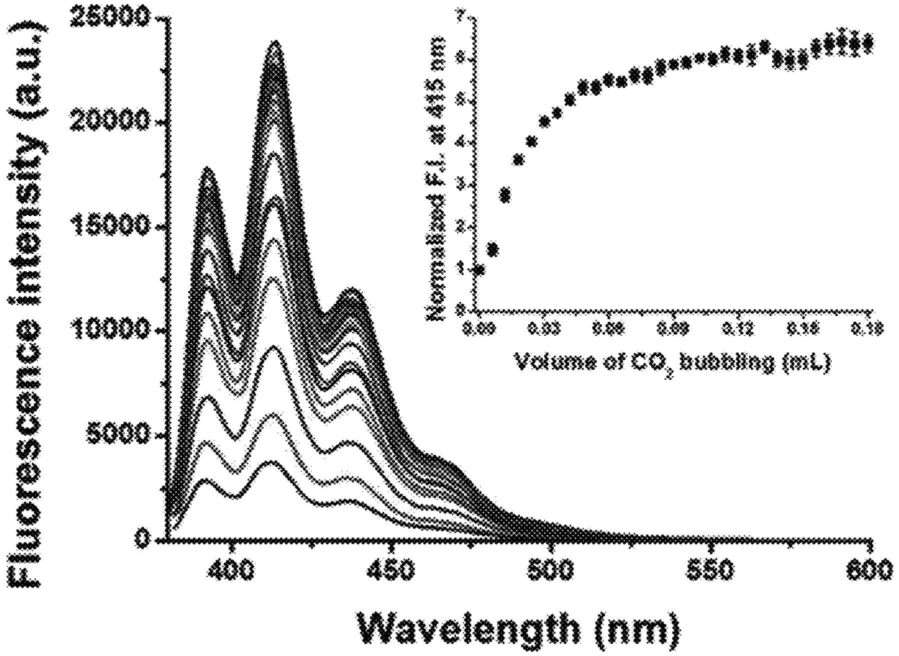
FIG. 18 shows a fluorescent spectrum obtained according to a carbon dioxide volume used to bubble a compound (Formula 2) prepared in Preparation Example 1. The graph inserted in FIG. 18 shows normalized fluorescent intensities at 415 nm according to the carbon dioxide volume used in the bubbling process.

FIG. 18 shows a fluorescent spectrum obtained according to a carbon dioxide volume used to bubble a compound (Formula 2) prepared in Preparation Example 1. The graph inserted in FIG. 18 shows normalized fluorescent intensities at 415 nm according to the carbon dioxide volume used in the bubbling process.

Here, the carbon dioxide volume was from 0.03 ml to 0.18 ml, and, starting from the black line providing 0.03 ml, positions of lines increased as the provided carbon dioxide volume increased until 0.18 ml (a line at the highest position).

In a graph shown in FIG. 18, each of the lines is the same with a point of fluorescence intensity according to the carbon dioxide volume shown in the inserted graph.

As shown in FIG. 18, it may be confirmed that a fluorescence intensity of the compound (Formula 2) prepared in Preparation Example 1 proportionally increased to the carbon dioxide volume (which increased 0.006 ml at a time). When about 0.06 ml of the carbon dioxide was bubbled, it was confirmed that the solution was saturated.

Figure 19:
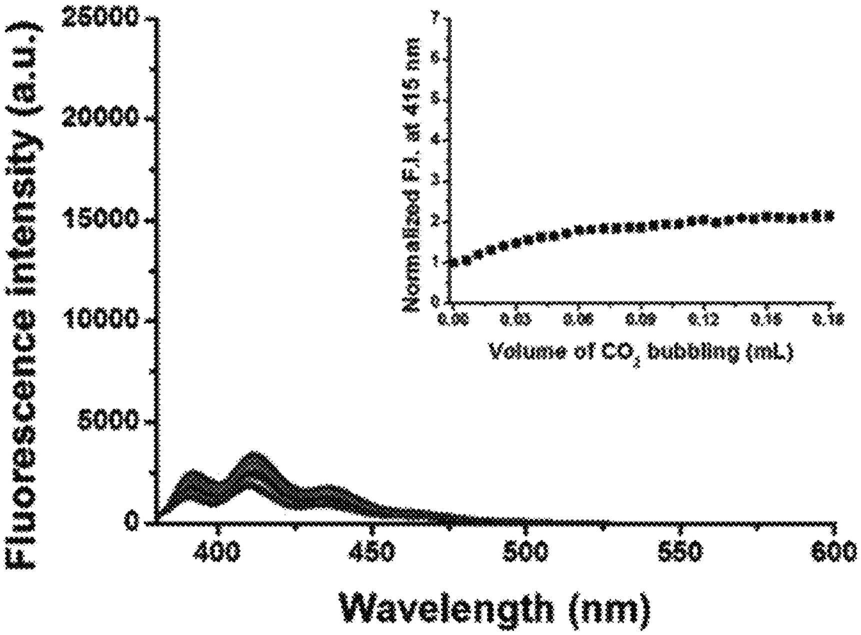
FIG. 19 shows a fluorescent spectrum obtained according to a carbon dioxide volume used to bubble a compound (Formula 7) prepared in Comparative Example 1. The graph inserted in FIG. 19 shows normalized fluorescent intensities at 415 nm according to the carbon dioxide volume used in the bubbling process.

FIG. 19 shows a fluorescent spectrum measured according to a carbon dioxide volume used to bubble a compound (Formula 7) prepared in Comparative Example 1. The graph inserted in FIG. 19 shows normalized fluorescent intensities at 415 nm according to the carbon dioxide volume used in the bubbling process.

Here, the carbon dioxide volume was from 0.00 ml to 0.18 ml, and, starting from the black line providing 0.00 ml, positions of lines had no change as the provided carbon dioxide volume increased until 0.18 ml (a line at the highest position).

In a graph shown in FIG. 19, each of the lines is the same with a point of fluorescence intensity according to the carbon dioxide volume shown in the inserted graph.

As shown in FIG. 19, it may be confirmed that a fluorescence intensity of the compound increased according to the carbon dioxide volume, but the sensitivity was significantly low compared to that of the compound (Formula 2) prepared in Preparation Example 1 with carbamic acid stabilization effect due to the intramolecular hydrogen bond in the compound (Formula 2).

Figure 20:
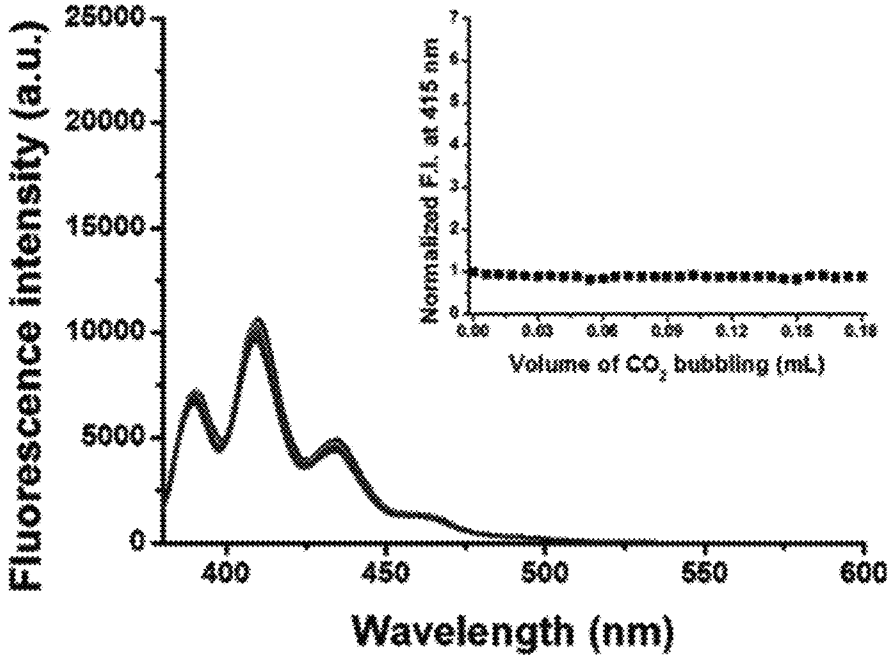
FIG. 20 shows a fluorescent spectrum obtained according to a carbon dioxide volume used to bubble a compound (Formula 8) prepared in Comparative Example 2. The graph inserted in FIG. 19 shows normalized fluorescent intensities at 415 nm according to the carbon dioxide volume used in the bubbling process.

FIG. 20 shows a fluorescent spectrum measured according to a carbon dioxide volume used to bubble a compound (Formula 8) prepared in Comparative Example 2. The graph inserted in FIG. 19 shows normalized fluorescent intensities at 415 nm according to the carbon dioxide volume used in the bubbling process.

Here, the carbon dioxide volume was from 0.00 ml to 0.18 ml, and, starting from the black line providing 0.00 ml, positions of lines had no change as the provided carbon dioxide volume increased until 0.18 ml (a line at the highest position).

In a graph shown in FIG. 20, each of the lines is the same with a point of fluorescence intensity according to the carbon dioxide volume shown in the inserted graph.

As shown in FIG. 20, it may be confirmed that the compound (Formula 8) prepared in Comparative Example 2 did not have any change according to the carbon dioxide volume.

In this regard, it may be confirmed that the fluorescence intensity of the compound (Formula 2) prepared in Preparation Example 1 according to the present invention was significantly changed according to the carbon dioxide volume by stabilizing carbamic acid due to the hydrogen bond in the molecule, whereas the compounds (Formula 7 and Formula 8) of Comparative Examples 1 and 2 that were quantitatively provided with carbon dioxide at the same concentration level had almost no fluorescence change.

Experimental Example 2

3 ml (50 μM) of the compound (Formula 2) synthesized from Preparation Example 1 was bubbled with 1.8 ml of a gas mixture including carbon dioxide ($CO_2$) and nitrogen ($N_2$) ($CO_2$:$N_2$=1:9) to obtain a compound represented by Formula 5.

Then, the solution including the compound represented by Formula 5 was bubbled with 10 ml of nitrogen gas at a flow rate of 30 ml/min, and the fluorescent spectrum change was observed. That is, the fluorescence change according to a volume increase of nitrogen in the compound represented by Formula 5 was confirmed.

Here, the measurement of fluorescent spectrum was performed under the same conditions used in 2) of Experimental Example 1.

[Formula 5]

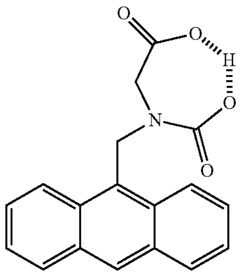

Figure 21:
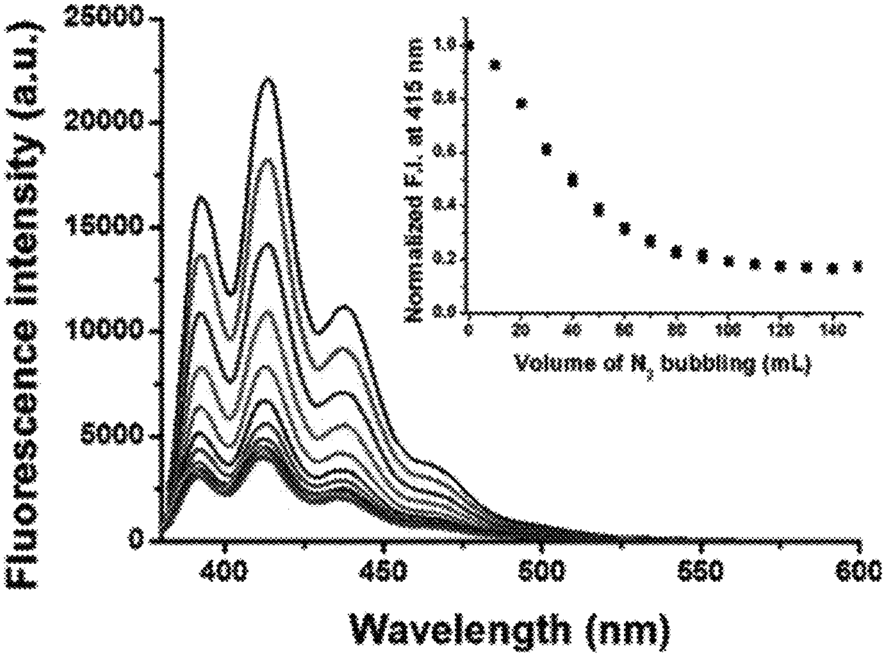
FIG. 21 shows a fluorescent spectrum of a compound obtained by bubbling the compound (Formula 2) synthesized in Preparation Example 1 with carbon dioxide, according to a nitrogen volume. The graph inserted in FIG. 21 shows normalized fluorescent intensities at 415 nm according to the nitrogen volume.

FIG. 21 shows a fluorescent spectrum of a compound obtained by bubbling the compound (Formula 2) synthesized in Preparation Example 1 with carbon dioxide, according to a nitrogen volume. The graph inserted in FIG. 21 shows normalized fluorescent intensities at 415 nm according to the nitrogen volume.

Here, the nitrogen volume was from 0.00 ml to 150 ml, and, starting from the black line providing 0.00 ml, positions of lines decreased as the nitrogen volume increased until 150 ml (a line at the highest position).

In a graph shown in FIG. 21, each of the lines is the same with a point of fluorescence intensity according to the carbon dioxide volume shown in the inserted graph.

As shown in FIG. 21, it may be confirmed that a fluorescence intensity of the compound (Formula 5) prepared by bubbling the compound (Formula 2) in Preparation Example 1 with carbon dioxide proportionally decreased to the nitrogen volume used in the nitrogen bubbling process.

When the compound (Formula 5) obtained by being bubbled with carbon dioxide was bubbled with about 150 ml of nitrogen, it was confirmed that the fluorescence intensity extinct to the level before bubbling the compound (Formula 2) prepared in Preparation Example 1 with carbon dioxide.

In this regard, it may be confirmed that when the compound (Formula 2) prepared in Preparation Example 1 is bubbled with carbon dioxide, the compound (Formula 5) may be prepared, and when the compound (Formula 5) is injected or bubbled with nitrogen, the carbon dioxide is separated from the compound (Formula 5) which then returns to the compound (Formula 2) prepared in Preparation Example 1.

That is, it may be confirmed that the carbon dioxide sensor according to the present invention is a renaturable carbon dioxide sensor through nitrogen injection, that is, a sensor capable of reversibly attaching and detaching carbon dioxide.

Experimental Example 3

In order to confirm whether the reversibility found in Experimental Example 2 may be repeated or not, fluorescent spectrum change was observed while bubbling 3 ml (50 μM) of the compound (Formula 2) prepared in Preparation Example 1 with 1.8 ml of a gas mixture including carbon dioxide ($CO_2$) and nitrogen ($N_2$) ($CO_2$:$N_2$=1:9) and 150 ml nitrogen gas, alternately.

Here, the measurement of fluorescent spectrum was performed under the same conditions used in 2) of Experimental Example 1.

Figure 22:
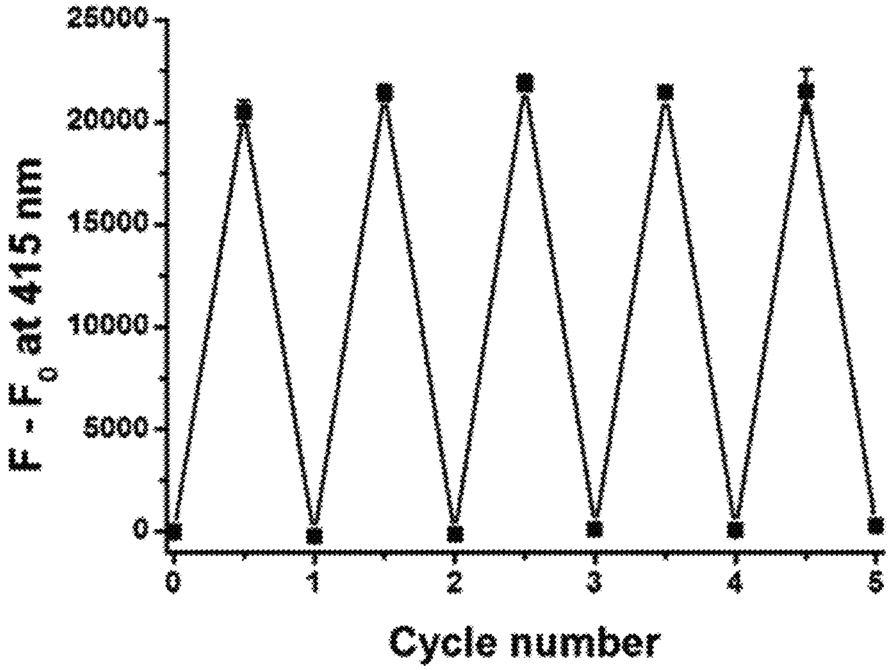
FIG. 22 shows a fluorescent spectrum that is measured by alternately bubbling the compound (Formula 2) synthesized in Preparation Example 1 with 0.18 ml of carbon dioxide ($CO_2$) and 150 ml of nitrogen ($N_2$) gas.

FIG. 22 shows a fluorescent spectrum that is measured by alternately bubbling the compound (Formula 2) synthesized in Preparation Example 1 with 0.18 ml of carbon dioxide ($CO_2$) and 150 ml of nitrogen ($N_2$) gas.

As shown in FIG. 22, it may be confirmed that when 18 ml of carbon dioxide and 150 ml of nitrogen bubbling was repeated 5 times, the optical characteristics of the compound (Formula 2) prepared in Preparation Example 1 at the initial stage was maintained the same.

In this regard, it may be known that the reaction between the compound (Formula 2) prepared in Preparation Example 1 according to the present invention and carbon dioxide is a reversible reaction, and when the compound is used as a carbon dioxide sensor, the carbon dioxide sensor may be repeatedly re-used, not as a disposable.

Experimental Example 4

A carbon dioxide detection limit of the compound (Formula 2) prepared in Preparation Example 1 was calculated from the fluorescent spectrum according to carbon dioxide titration obtained from Experimental Example 1.

Here, in order to calculate the carbon dioxide detection limit, a mole of the carbon dioxide used in the bubbling process was calculated by using the ideal gas equation, a log was taken therefrom, and each of the normalized fluorescence intensities was plotted to obtain FIG. 21.

Figure 23:
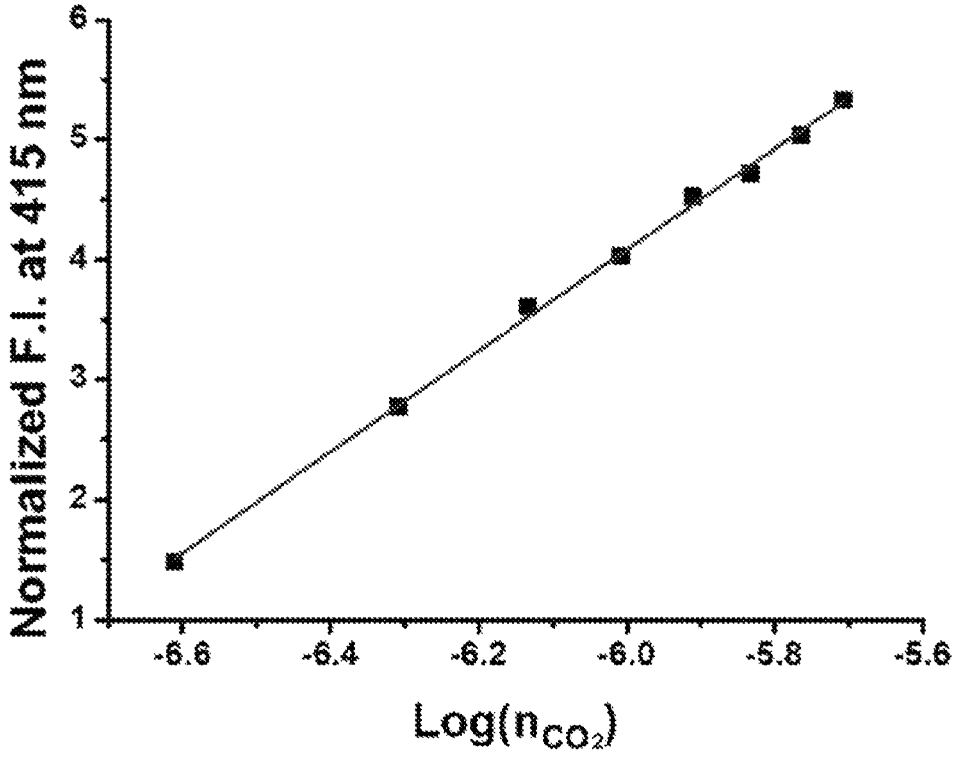
FIG. 23 shows a graph that illustrates the calculated result of carbon dioxide detection limit of the compound (Formula 2) synthesized in Preparation Example 1.

FIG. 23 shows a graph that illustrates the calculated result of carbon dioxide detection limit of the compound (Formula 2) synthesized in Preparation Example 1.

As a result of obtaining a detection limit mole of carbon dioxide by using FIG. 23 and converting the mole into a concentration in ppm, it was confirmed that the detection limit of the compound (Formula 2) prepared in Preparation Example 1 was 2.04 ppm.

The detection limit value is about 10 times or more sensitive than that of a conventional carbon dioxide fluorescence sensor.

Experimental Example 5

The compound (Formula 2) synthesized in Preparation Example 1 was dissolved in DMSO-$d_6$, the $^1$H-NMR spectrums before and after bubbling with carbon dioxide were obtained and compared.

Figure 24:
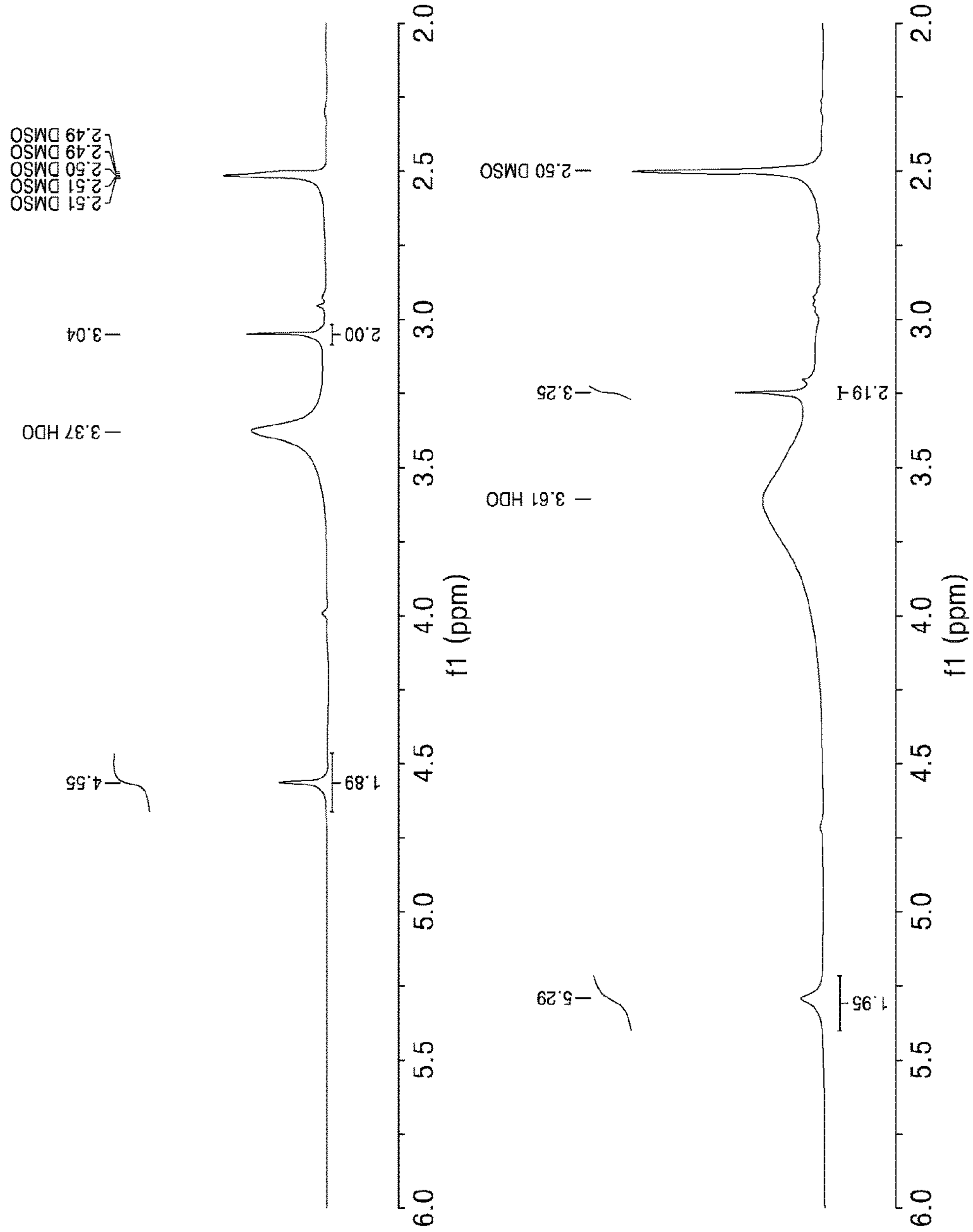
FIG. 24 shows a graph that illustrates the results of $^{1}$H-NMR (300 MHz) spectrum analysis from the spectroscopic analysis results of the compound (Formula 2) synthesized in Preparation Example 1 (a) before and (b) after being bubbled with carbon dioxide after being dissolved in DMSO-$d_6$.

FIG. 24 shows a graph that illustrates the results of $^1$H-NMR (300 MHz) spectrum analysis from the spectroscopic analysis results of the compound (Formula 2) synthesized in Preparation Example 1 (a) before and (b) after being bubbled with carbon dioxide after being dissolved in DMSO-do.

As shown in FIG. 24, the compound (Formula 2) synthesized in Preparation Example 1 had peaks corresponding to $CO_2$—$CH_2$—N (s=3.04 ppm) and N—$CH_2$-anthracene (s=4.55 ppm).

As carbon dioxide was injected to the compound (Formula 2) synthesized in Preparation Example 1, these peaks were shifted to $CO_2$—$CH_2$—N (s=3.25 ppm) and N—$CH_2$-anthracene (s=5.29 ppm), respectively.

That is, as the compound (Formula 2) and carbon dioxide react to form the compound (Formula 5), an additionally produced carbonyl group in a carbamic acid functional group serves as an electron withdrawing group, which is deemed as due to a decreased electron density of peripheral protons compared to that before the formation of the compound (Formula 5).

Experimental Example 6

Energy of each of the compound (Formula 2) prepared in Preparation Example 1, the compound (Formula 7) prepared in Comparative Example 1, the compound (Formula 8) prepared in Comparative Example 2, and the compounds (Formula 5, Formula 9, and Formula 10) that were prepared by reacting the compounds (Formula 2, Formula 7, and Formula 8) with carbon dioxide by using an ab initio quantum mechanical calculation.

Structure optimization of each of the compound (Formula 2) prepared in Preparation Example 1, the compound (Formula 7) prepared in Comparative Example 1, the compound (Formula 8) prepared in Comparative Example 2, and the compounds (Formula 5, Formula 9, and Formula 10) that were prepared by reacting the compounds (Formula 2, Formula 7, and Formula 8) with carbon dioxide had 6-311++ G(2d,p) as a basis set, and the Gaussian 03 program was performed thereon using a density functional theory (DFT).

In the calculation of the DFT, Becke's three-parameter exchange functional and Lee-Yang-Parr's correlation functional (B3LYP) were used.

A vibrational frequency analysis was performed to confirm whether the energy having a structure obtained by the structure optimization calculation was local minimum or not, and a single point energy calculation (MP2//B3LYP) was subsequently performed on the optimized structure obtained by using B3LYP using a MOller-Plesset second-order perturbation (MP2) method to obtain an accurate result.

Figure 25:
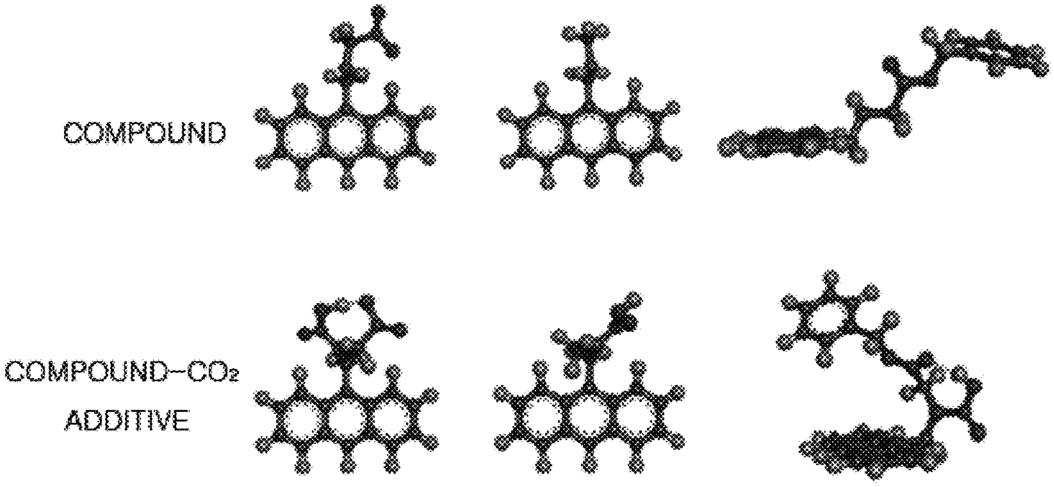
FIG. 25 shows optimized structures of the compound (Formula 2) prepared in Preparation Example 1, the compound (Formula 7) prepared in Comparative Example 1, the compound (Formula 8) prepared in Comparative Example 2, and compounds (Formula 5, Formula 9, and Formula 10) produced when the compounds (Formula 2, Formula 7, and Formula 8) reacted with carbon dioxide, according to the DFT calculation.

FIG. 25 shows optimized structures of the compound (Formula 2) prepared in Preparation Example 1, the compound (Formula 7) prepared in Comparative Example 1, the compound (Formula 8) prepared in Comparative Example 2, and compounds (Formula 5, Formula 9, and Formula 10) produced when the compounds (Formula 2, Formula 7, and Formula 8) reacted with carbon dioxide, according to the DFT calculation.

According to FIG. 25, the compound of Formula 5 and the compound of Formula 10 had atom changes in oxygen atom and hydrogen atom that were involved in the intramolecular hydrogen bond, which appeared at −0.79 e/+0.48 e and −0.60 e/+0.50 e, respectively.

In this regard, it may be confirmed that a strong intramolecular hydrogen bond was formed by a carboxylate group in the compound of Formula 5.

From the optimized structures shown in FIG. 25, binding energy between carbon dioxide and each of the compound (Formula 2) prepared in Preparation Example 1, the compound (Formula 7) prepared in Comparative Example 1, the compound (Formula 8) prepared in Comparative Example 2 is shown in Table 1.

TABLE 1

| ΔE (kcal/mol) | Compound of Formula 2 (Preparation Example 1) | Compound of Formula 7 (Comparative Example 1) | Compound of Formula 8 (Comparative Example 2) |
|---|---|---|---|
| $\Delta E_e$(B3LYP) | −12.1 | −1.1 | 4.6 |
| $\Delta E_0$(B3LYP) | −12.0 | 1.4 | 7.1 |
| $\Delta E_e$ (MP2//B3LYP) | −16.0 | −5.2 | −2.8 |
| $\Delta E_0$ (MP2//B3LYP) | −15.9 | −2.7 | −0.3 |

In Table 1, $\Delta E_e$ and $\Delta E_0$ denote before and after introducing zero-point vibration energy through the vibrational frequency analysis.

When the $\Delta E_0$ (MP2//B3LYP) values of the compound (Formula 2) prepared in Preparation Example 1, the compound (Formula 7) prepared in Comparative Example 1, the compound (Formula 8) prepared in Comparative Example 2 are compared, it may be known that the compound (Formula 2) prepared in Preparation Example 1 with carbon dioxide forms the most stable compound (Formula 5).

This result is deemed as due to stabilization caused by the intramolecular hydrogen bond as described above.

Experiment Example 7

8 types of amine compounds that have been used or studied as a conventional carbon dioxide adsorbent were selected (Table 2), and activities thereof were measured by using the compound of Formula 2 synthesized in Preparation Example 1. The results are shown in FIG. 26.

In order to compare with the activity result of the carbon dioxide adsorbent measured by using the carbon dioxide chemical sensor according to the present invention, activities of the carbon dioxide adsorbents were measured by thermal gravimetric analysis (TGA) that is commonly used as a conventional carbon dioxide adsorbent activity measuring method. The results are shown in Table 3.

The compound of Formula 2 synthesized in Preparation Example 1 was mixed with 5 mM of the carbon dioxide adsorbent so that the final concentration was 50 μM to prepare a mixture, and 3 ml the mixture was bubbled with 0.048 ml of carbon dioxide to observe its fluorescent spectrum.

Figure 26:
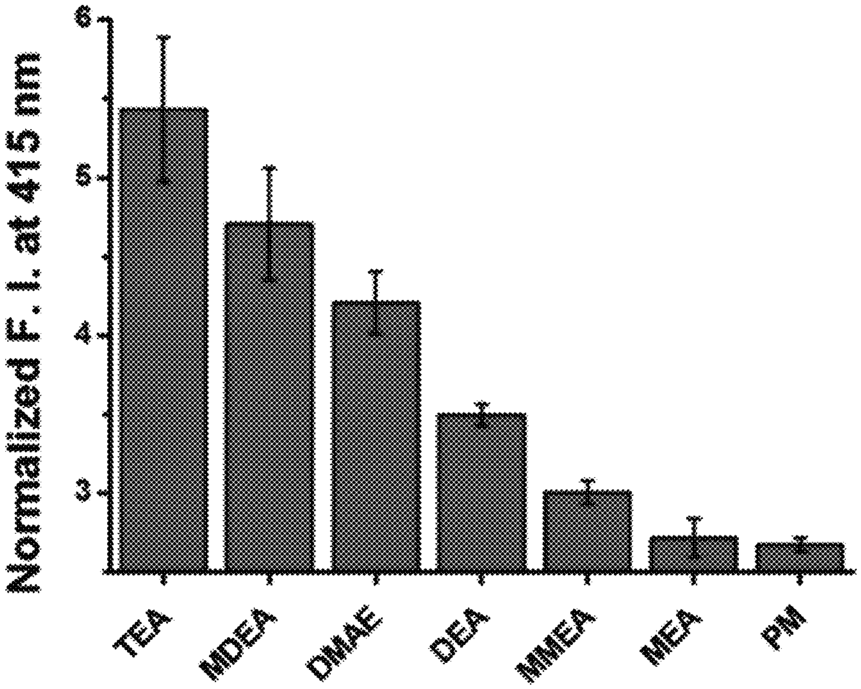
FIG. 26 shows a graph of normalized fluorescent intensities at 415 nm after mixing a carbon dioxide adsorbent and the compound of Preparation Example 1 and providing the same amount of carbon dioxide to measure relative carbon dioxide adsorbing performance with respect to 8 different types of conventional carbon dioxide adsorbents by using the compound of Formula 2 synthesized in Preparation Example 1.

Then, the fluorescence intensity at 415 nm was normalized to obtain a graph, and the graph is shown in FIG. 26.

TABLE 2

| Name | Structural Formula |
|---|---|
| TEA (triethanolamine) | 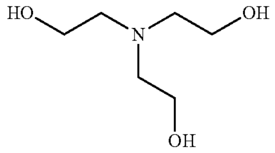 |
| MDEA (N-methyldiethanolamine) | 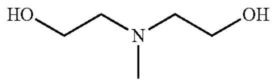 |

TABLE 2-continued

| Name | Structural Formula |
|---|---|
| DMEA (dimethylethanmolamine) | 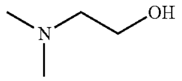 |
| DEA (diethanolamine) | 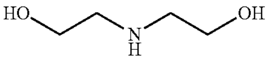 |
| MMEA (N-methylethanolamine) | 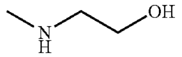 |
| MEA (monoethanolamine) | 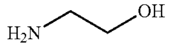 |
| PM (2-piperidinemethanol) | 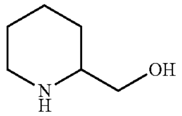 |

TABLE 3

| Carbon dioxide adsorbent | Absorption capacity ($n_{CO2}/n_{amine}$) | Initial adsorption rate ($n_{CO2}/n_{amine}$) | Absorption capacity × initial adsorption rate |
|---|---|---|---|
| TEA | 0.24 | — | — |
| MDEA | 0.4 | 0.003 | 0.0012 |
| DMEA | 0.92 | 0.002 | 0.0018 |
| DEA | 0.6 | 0.008 | 0.0048 |
| MMEA | 0.63 | 0.012 | 0.0076 |
| MEA | 0.56 | 0.014 | 0.0078 |
| PM | 1 | 0.012 | 0.0120 |

FIG. 26 shows a graph of normalized fluorescent intensities at 415 nm after mixing a carbon dioxide adsorbent and the compound of Preparation Example 1 and providing the same amount of carbon dioxide to measure relative carbon dioxide adsorbing performance with respect to 8 different types of conventional carbon dioxide adsorbents by using the compound of Formula 2 synthesized in Preparation Example 1.

According to FIG. 26, as a result of comparing the normalized fluorescence intensities measured by using the compound of Formula 2 synthesized in Preparation Example 1, relative absorption capacity of the carbon dioxide adsorbents were confirmed in the order of PM, MEA, MMEA>DEA>DMEA, MDEA>TEA.

This result confirmed that it showed the same tendency with that of absorption capacity x initial adsorption rate in the results (Table 3) which measured the carbon dioxide adsorbents by using TGA, as a conventional carbon dioxide adsorbent activity measuring method commonly used in the art.

It was confirmed that relative absorption capacity of the adsorbents may be measured while taking both factors, which are absorption capacity and initial absorption rate, into account of both factors by only using fast and convenient fluorescence analysis on the carbon dioxide adsorbent using the compound of Formula 2 synthesized in Preparation Example 1.

That is, the carbon dioxide adsorbents may be rapidly and easily distinguished according to their relative capacities by using an evaluation method using the compound of Formula 2 synthesized in Preparation Example 1, and this may be applied to high throughput screening that rapidly selects only the carbon dioxide adsorbents having good absorbance capacity from a number of carbon dioxide adsorbent candidates.

Experiment Example 8

3 ml (75 μM) of the compound (Formula 3) synthesized in Preparation Example 2 was bubbled with a gas mixture including carbon dioxide ($CO_2$) and nitrogen ($N_2$) ($CO_2$:$N_2$=1:9) until a volume of carbon dioxide was 0.9 ml, and the UV/vis light-absorptivity change was observed. The result is shown in FIG. 28.

Here, the carbon dioxide volume changed from 0.00 ml to 0.9 ml, and, starting from the black line providing 0.00 ml, positions of lines changed as the provided carbon dioxide volume increased until 0.9 ml (a light blue line).

Figure 29:
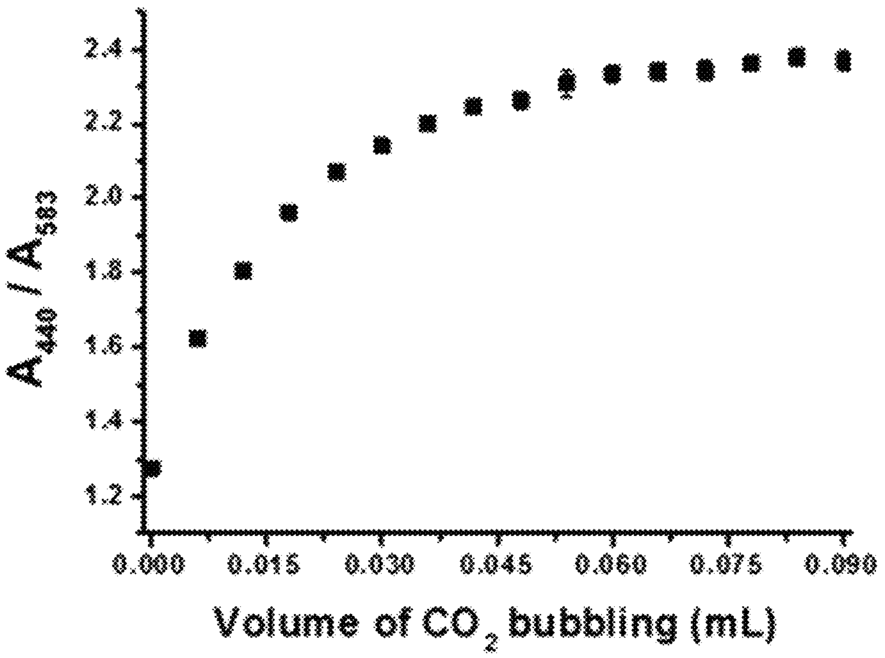
FIG. 29 shows a graph of the calculated results of a ratio ($A_{440}/A_{583}$) of a light-absorption band at 440 nm ($A_{440}$) and a light-absorption band at 583 nm ($A_{583}$) measured from the UV/vis light-absorptivity graph of the compound (Formula 3) synthesized in Preparation Example 2 according to a carbon dioxide concentration.

Also, a ratio ($A_{440}/A_{583}$) of a light-absorption band at 440 nm ($A_{440}$) and a light-absorption band at 583 nm ($A_{583}$) measured from the UV/vis light-absorptivity graph of the compound (Formula 3) synthesized in Preparation Example 2 according to a carbon dioxide concentration was calculated, and the results are shown in FIG. 29.

Figure 28:
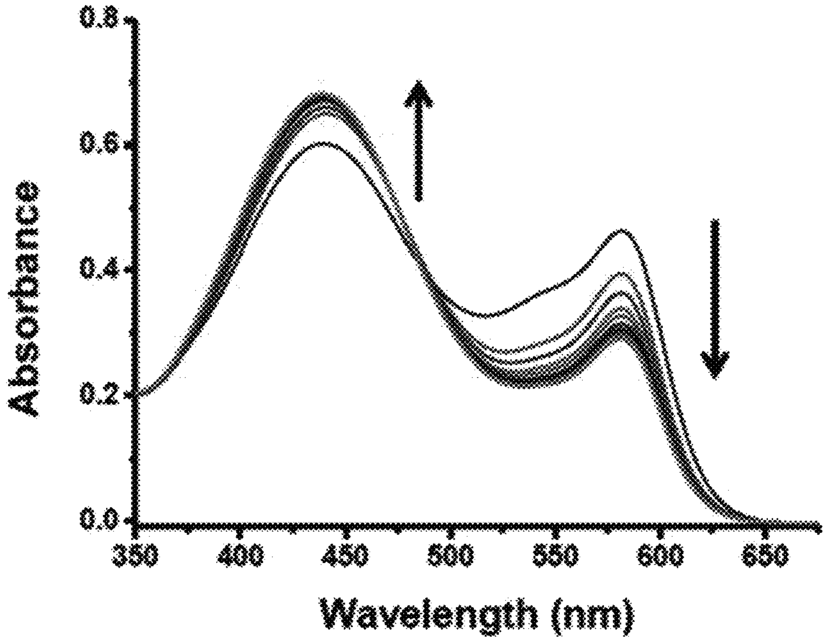
FIG. 28 shows a graph of UV/vis light-absorptivity of the compound (Formula 3) synthesized in Preparation Example 2 according to a carbon dioxide concentration.

As shown in FIG. 28, it was confirmed that an intensity of the light-absorption band within the wavelength range of 500 to 600 nm decreased as an amount of the carbon dioxide used for the compound (Formula 3) synthesized in Preparation Example 2.

On the other hand, it may be known that the intensity of the light-absorption band within the wavelength range of 400 to 450 nm increases, and this phenomenon, as shown in FIG. 27, may be confirmed with naked eye through the color change of the compound (Formula 3) of Preparation Example 2 from red to yellow.

Also, as shown in FIG. 29, it was confirmed that the ratio ($A_{440}/A_{583}$) of a light-absorption band at 440 nm ($A_{440}$) and a light-absorption band at 583 nm ($A_{583}$) calculated per carbon dioxide concentration and measured from the UV/vis light-absorptivity graph as the maximum light-absorption band proportionally increases as the carbon dioxide concentration increases.

Therefore, the carbon dioxide sensor using the compound synthesized in Preparation Example 2 according to the present invention may allow the change according to the detection of carbon dioxide by color change with naked eye, and thus the sensor may be effectively used as a carbon dioxide detection sensor.

Experimental Example 9

3 ml (75 μM) of the compound (Formula 3) synthesized in Preparation Example 2 was bubbled with a gas mixture including carbon dioxide ($CO_2$) and nitrogen ($N_2$) ($CO_2$:$N_2$=1:9) until a volume of carbon dioxide was 0.9 ml, and the UV/vis light-absorptivity change was observed while bubbling with nitrogen ($N_2$) gas. The result is shown in FIG. 30.

Here, the nitrogen volume changed from 0.00 ml to 33 ml, and, starting from the black line providing 0.00 ml, positions of lines changed as the provided carbon dioxide volume increased until 30 ml (a blue line).

Figure 31:
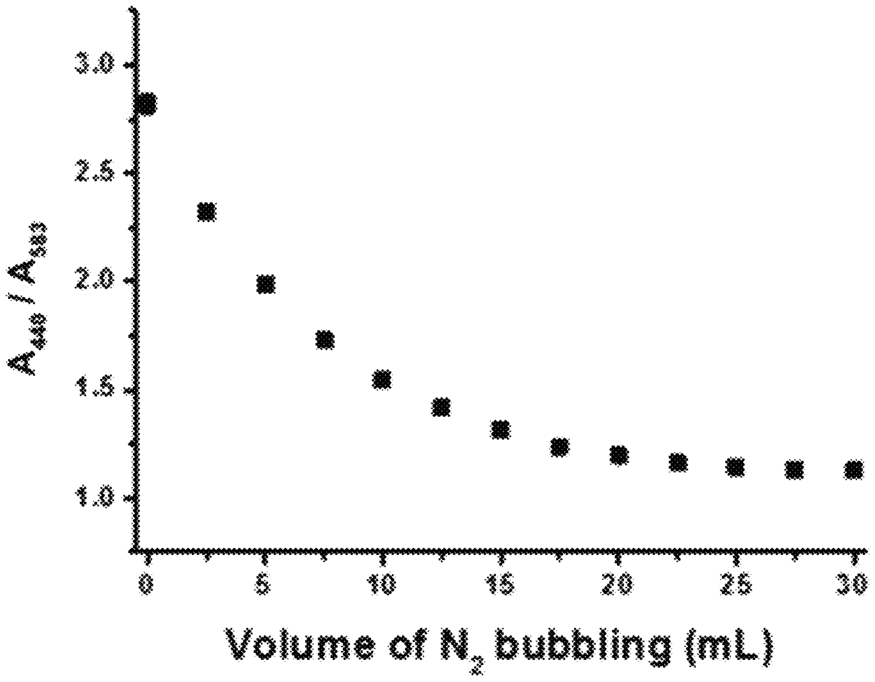
FIG. 31 shows a graph of the calculated results of a ratio ($A_{440}/A_{583}$) of a light-absorption band at 440 nm ($A_{440}$) and a light-absorption band at 583 nm ($A_{583}$) measured from the UV/vis light-absorptivity graph of the compound (Formula 3) synthesized in Preparation Example 2 according to a nitrogen concentration.

Also, a ratio ($A_{440}/A_{583}$) of a light-absorption band at 440 nm ($A_{440}$) and a light-absorption band at 583 nm ($A_{583}$) measured from the UV/vis light-absorptivity graph of the compound (Formula 3) synthesized in Preparation Example 2 according to a carbon dioxide concentration was calculated, and the results are shown in FIG. 31.

Figure 30:
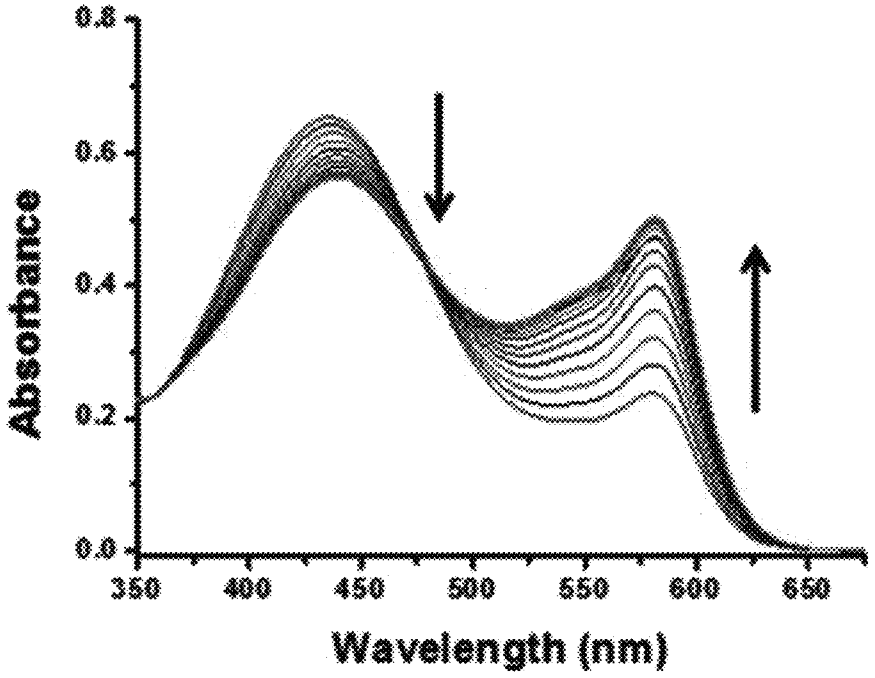
FIG. 30 shows a graph of the measured UV/vis light-absorptivity of the compound (Formula 3) synthesized in Preparation Example 2 that is bubbled with carbon dioxide and the bubbled with nitrogen.

As shown in FIG. 30, the compound (Formula 3) synthesized from Preparation Example 2 was bubbled with carbon dioxide, and then bubbled with nitrogen, and it was confirmed that as the bubbling processes increased, the intensity of the light-absorptivity within a wavelength range of 500 to 600 nm increased.

On the other hand, it may be known that the intensity of the light-absorption band of 400 to 450 nm decreased, and this phenomenon, as shown in FIG. 27, may be confirmed by color change observed with naked eye, where the color changes from red to yellow when the compound (Formula 3) of Preparation Example 2 reacts with carbon dioxide, and the color turns back to red when nitrogen is injected.

Also, as shown in FIG. 31, it was confirmed that the ratio ($A_{440}/A_{583}$) of a light-absorption band at 440 nm ($A_{440}$) and a light-absorption band at 583 nm ($A_{583}$) calculated per carbon dioxide concentration and measured from the UV/vis light-absorptivity graph as the maximum light-absorption band decreases as the nitrogen concentration increases.

Therefore, the carbon dioxide sensor using the compound synthesized in Preparation Example 2 according to the present invention may allow the change according to the detection of carbon dioxide followed by returning back to the original compound via the nitrogen bubbling process by color change with naked eye, and thus the sensor may be effectively used as a carbon dioxide detection sensor after detecting carbon dioxide.

What is claimed is:

1. A carbon dioxide sensor of an on/off type, the carbon dioxide sensor comprising (i) a carbon dioxide adsorbent material free of a chromophore; and (ii) a compound represented by Formula 1:

[Formula 1]

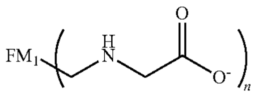

wherein, in Formula 1, $FM_1$ is any one selected from compounds represented by Structural Formula 1, and n is a real number of 1 to 2:

[Structural Formula 1]

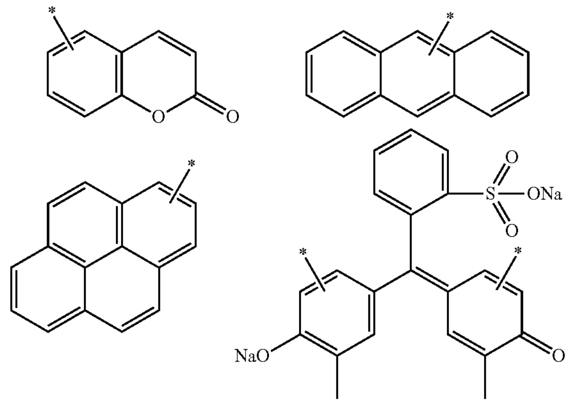

-continued

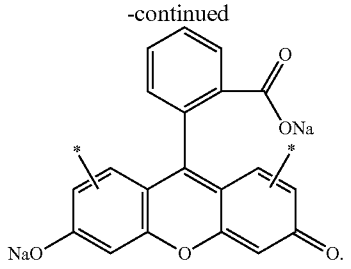

2. The carbon dioxide sensor of claim 1, wherein the (i) carbon dioxide adsorbent material free of a chromophore is any one selected from triethanolamine (TEA), N-methyl di ethanol amine (MDEA), dimethylethanmolamine (DMEA), diethanolamine (DEA), N-methylethanolamine (MMEA), monoethanolamine (MEA), and 2-piperidinemethanol (PM).

3. The carbon dioxide sensor of claim 1, wherein a carbon dioxide affinity of the (i) carbon dioxide adsorbent material free of a chromophore is higher than a carbon dioxide affinity of the (ii) compound represented by Formula 1.

4. A method of detecting carbon dioxide, the method comprising:

I) exposing the carbon dioxide sensor of claim 1 to a sample comprising carbon dioxide;

II) allowing the carbon dioxide sensor and carbon dioxide in the sample to react through the exposing in step I) to form a compound represented by Formula 4; and III) measuring light-absorptivity or fluorescence change of the compound represented by Formula 4 formed in step II),

[Formula 4]

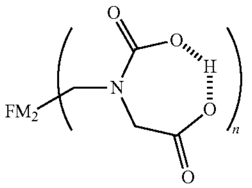

wherein, in Formula 4, $FM_2$ is any one selected from compounds represented by Structural Formula 2, and n is a real number of 1 to 2:

[Structural Formula 2]

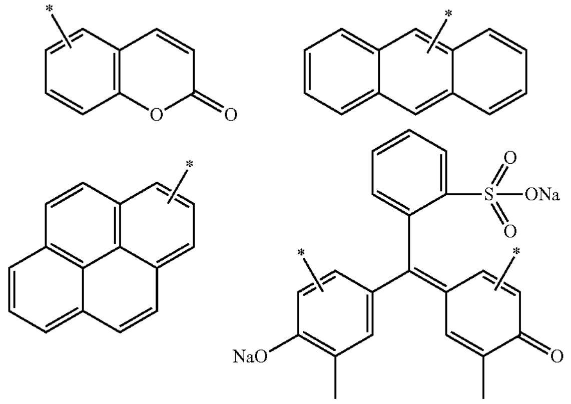

-continued

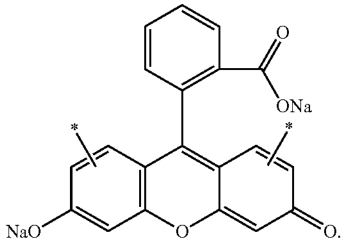

5. A method of regenerating the carbon dioxide sensor of claim 1, the method comprising:

I) detecting carbon dioxide with the carbon dioxide sensor of claim 1 by converting the compound of claim 1 represented by Formula 1 to a compound represented by Formula 4 by allowing the compound represented by Formula 1 to react with carbon dioxide;

II) converting the compound represented by Formula 4 to the compound represented by Formula 1 by separating carbon dioxide from the compound represented by Formula 4,

[Formula 4]

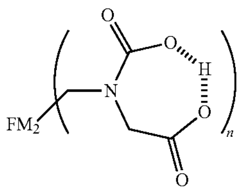

wherein, in Formula 4, $FM_2$ is any one selected from compounds represented by Structural Formula 2, and n is a real number of 1 to 2:

[Structural Formula 2]

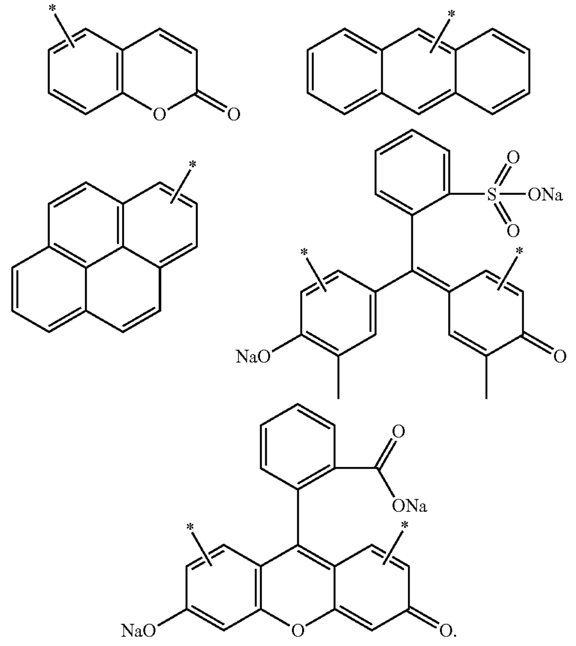

6. The method of claim 5, wherein, in step II), nitrogen is injected to convert the compound represented by Formula 4 to the compound represented by Formula 1 by separating carbon dioxide from the compound represented by Formula 4.

7. The method of claim 6, wherein, in step II), 100 to 200 ml of the nitrogen is injected based on 50 μM of the compound represented by Formula 4.

* * * * *